United States Patent
Hlavka et al.

(10) Patent No.: US 10,548,662 B2
(45) Date of Patent: Feb. 4, 2020

(54) METHODS AND DEVICES FOR TREATING PELVIC CONDITIONS

(71) Applicant: Hologic, Inc., Marlborough, MA (US)

(72) Inventors: Edwin J. Hlavka, Minneapolis, MN (US); Thomas V. Ressemann, Edina, MN (US); Eric Whitbrook, St. Paul, MN (US); John Christian Knudson, Minnetonka, MN (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/113,280

(22) Filed: Aug. 27, 2018

(65) Prior Publication Data

US 2018/0360530 A1 Dec. 20, 2018

Related U.S. Application Data

(63) Continuation of application No. 14/720,581, filed on May 22, 2015, now Pat. No. 10,058,381.

(60) Provisional application No. 62/002,742, filed on May 23, 2014.

(51) Int. Cl.
*A61N 1/36* (2006.01)
*A61B 18/14* (2006.01)
*A61N 1/05* (2006.01)
*A61B 18/18* (2006.01)
*A61B 18/00* (2006.01)

(52) U.S. Cl.
CPC ........ *A61B 18/1485* (2013.01); *A61N 1/0514* (2013.01); *A61N 1/36007* (2013.01); *A61B 18/1815* (2013.01); *A61B 2018/00291* (2013.01); *A61B 2018/00434* (2013.01); *A61B 2018/00523* (2013.01); *A61B 2018/00577* (2013.01); *A61B 2018/00815* (2013.01); *A61B 2018/00821* (2013.01); *A61B 2018/00982* (2013.01); *A61B 2018/1467* (2013.01); *A61B 2018/1475* (2013.01); *A61B 2218/002* (2013.01)

(58) Field of Classification Search
CPC ...... A61B 18/1485; A61B 2018/00517; A61B 2018/00559; A61B 2018/00291; A61B 2018/00523; A61B 2018/00577; A61B 2018/1475; A61N 1/36007; A61N 1/0514
See application file for complete search history.

(56) References Cited

U.S. PATENT DOCUMENTS

| | | |
|---|---|---|
| 5,342,353 A | 8/1994 | Allen |
| 5,370,675 A | 12/1994 | Edwards |
| 5,667,488 A | 9/1997 | Lundquist et al. |

(Continued)

FOREIGN PATENT DOCUMENTS

| | | |
|---|---|---|
| AU | 2010/319333 | 11/2010 |
| CN | 102256560 | 11/2011 |

(Continued)

OTHER PUBLICATIONS

Chinese Patent Office, Office Action dated Jan. 4, 2016, in Chinese Patent Application No. 201280046659, 21 pages.

(Continued)

*Primary Examiner* — Tammie K Marlen
(74) *Attorney, Agent, or Firm* — Vista IP Law Group LLP

(57) ABSTRACT

A device and method that provides a minimally-invasive approach to performing treatments on soft tissue, such as that found in the bladder. The device is useful for manipulating tissue such that treatment tools can be inserted into the tissue at a controlled depth.

20 Claims, 27 Drawing Sheets

(56) References Cited

U.S. PATENT DOCUMENTS

| | | |
|---|---|---|
| 5,672,153 A | 9/1997 | Lax et al. |
| 5,964,727 A | 10/1999 | Edwards et al. |
| 6,091,995 A | 7/2000 | Ingle et al. |
| 6,129,726 A | 10/2000 | Edwards et al. |
| 6,190,353 B1 | 2/2001 | Makower et al. |
| 6,216,704 B1 | 4/2001 | Ingle et al. |
| 6,231,518 B1 | 5/2001 | Grabek et al. |
| 6,325,798 B1 | 12/2001 | Edwards et al. |
| 6,419,653 B2 | 7/2002 | Edwards et al. |
| 6,425,877 B1 | 7/2002 | Edwards |
| 6,607,525 B2 | 8/2003 | Franco |
| 6,610,054 B1 | 8/2003 | Edwards et al. |
| 6,626,930 B1 | 9/2003 | Allen et al. |
| 6,632,193 B1 | 10/2003 | Davison et al. |
| 6,692,480 B1 | 2/2004 | Bush |
| 6,692,490 B1 | 2/2004 | Edwards |
| 6,852,091 B2 | 2/2005 | Edwards et al. |
| 6,960,205 B2 | 11/2005 | Jahns et al. |
| 7,818,039 B2 | 10/2010 | Jahns et al. |
| 8,197,504 B2 | 6/2012 | Stokes |
| 8,641,711 B2 | 2/2014 | Kelly et al. |
| 8,657,814 B2 | 2/2014 | Werneth et al. |
| 8,684,998 B2 | 4/2014 | Demarais et al. |
| 8,721,632 B2 | 5/2014 | Hoey et al. |
| 8,740,896 B2 | 6/2014 | Zarins et al. |
| 8,758,337 B2 | 6/2014 | Skwarek et al. |
| 8,771,267 B2 | 7/2014 | Kunis et al. |
| 8,771,269 B2 | 7/2014 | Sherman et al. |
| 8,790,281 B2 | 7/2014 | Diederich et al. |
| 8,840,625 B2 | 9/2014 | Adams et al. |
| 9,561,067 B2 | 2/2017 | Sharma |
| 2002/0002372 A1 | 1/2002 | Jahns et al. |
| 2002/0003244 A1 | 1/2002 | Tooher et al. |
| 2002/0032441 A1 | 3/2002 | Ingle et al. |
| 2002/0188169 A1 | 12/2002 | Krammerer et al. |
| 2002/0193851 A1 | 12/2002 | Silverman |
| 2003/0032860 A1 | 2/2003 | Avni et al. |
| 2003/0181904 A1 | 9/2003 | Levine |
| 2004/0021579 A1 | 2/2004 | Oursler et al. |
| 2004/0059389 A1 | 3/2004 | Chornenky |
| 2004/0153098 A1 | 8/2004 | Chin et al. |
| 2004/0186468 A1 | 9/2004 | Edwards |
| 2004/0215179 A1 | 10/2004 | Swoyer et al. |
| 2005/0096638 A1 | 5/2005 | Starkebaum |
| 2005/0261673 A1 | 11/2005 | Bonner |
| 2006/0089635 A1 | 4/2006 | Young et al. |
| 2007/0014784 A1 | 1/2007 | Nayak |
| 2007/0112340 A1 | 5/2007 | Thomas et al. |
| 2007/0179535 A1 | 8/2007 | Morissey |
| 2009/0069803 A1 | 3/2009 | Starkebaum |
| 2009/0171315 A1 | 7/2009 | Versi |
| 2010/0049186 A1 | 2/2010 | Ingle et al. |
| 2010/0121269 A1 | 5/2010 | Goldenberg |
| 2010/0174306 A1 | 7/2010 | Mitelberg et al. |
| 2010/0256446 A1 | 10/2010 | Raju |
| 2011/0112434 A1 | 5/2011 | Ghabrial et al. |
| 2011/0270243 A1 | 11/2011 | Skarda et al. |
| 2012/0047417 A1 | 2/2012 | Koike |
| 2012/0048417 A1 | 3/2012 | Smith et al. |
| 2012/0048419 A1 | 3/2012 | Giribona et al. |
| 2012/0123411 A1 | 5/2012 | Ibrahim et al. |
| 2013/0018281 A1 | 1/2013 | Nagale et al. |
| 2013/0030249 A1 | 1/2013 | Vazales et al. |
| 2013/0066308 A1 | 3/2013 | Landman |
| 2013/0072855 A1 | 3/2013 | Sherry et al. |
| 2013/0090640 A1 | 4/2013 | Nagale et al. |
| 2013/0090648 A1 | 4/2013 | Nagale et al. |
| 2013/0172864 A1 | 7/2013 | Ibrahim et al. |
| 2014/0012256 A1 | 1/2014 | Deem et al. |
| 2014/0018786 A1 | 1/2014 | Van Wyk et al. |
| 2014/0025055 A1 | 1/2014 | Burnett et al. |
| 2014/0031810 A1 | 1/2014 | Mahvi et al. |
| 2014/0039356 A1 | 1/2014 | Sachs et al. |
| 2014/0012247 A1 | 2/2014 | Bakos et al. |
| 2014/0036356 A1 | 2/2014 | Feinbloom et al. |
| 2014/0039491 A1 | 2/2014 | Bakos et al. |
| 2014/0081257 A1 | 3/2014 | Ghoniem |
| 2014/0148798 A1 | 5/2014 | Sachs et al. |
| 2014/0163548 A1 | 6/2014 | Christian |
| 2014/0200568 A1 | 7/2014 | Sharma |
| 2014/0207136 A1 | 7/2014 | De La Rama et al. |
| 2014/0257272 A1 | 9/2014 | Clark, III et al. |
| 2014/0276593 A1 | 9/2014 | Nagale et al. |
| 2014/0276726 A1 | 9/2014 | Model |
| 2016/0030107 A1 | 2/2016 | Herbst et al. |
| 2018/0228540 A1 | 8/2018 | Sachs et al. |

FOREIGN PATENT DOCUMENTS

| | | |
|---|---|---|
| CN | 103764225 | 4/2014 |
| CN | 104080418 | 10/2014 |
| EP | 2155093 | 2/2010 |
| EP | 2349045 | 8/2011 |
| EP | 2759276 | 7/2014 |
| EP | 2813192 | 12/2014 |
| JP | 2001/514921 | 9/2001 |
| JP | 2003/510126 | 3/2003 |
| JP | 2009/532074 | 9/2009 |
| JP | 2009/297527 | 12/2009 |
| JP | 2010/533036 | 10/2010 |
| JP | 2006/334398 | 12/2016 |
| WO | WO 2004/010843 | 2/2004 |
| WO | WO 2013/016588 | 1/2013 |
| WO | WO 2013/016590 | 1/2013 |
| WO | WO 2013/160772 | 10/2013 |
| WO | WO 2014/004965 | 1/2014 |
| WO | WO 2014/022379 | 2/2014 |
| WO | WO 2014/022436 | 2/2014 |
| WO | WO 2014/025394 | 2/2014 |
| WO | WO 2014/026028 | 2/2014 |
| WO | WO 2014/113724 | 7/2014 |

OTHER PUBLICATIONS

European Examination in Application No. 12746192.9, dated Dec. 15, 2017, 4 pages.

Extended European Search Report in Application No. 15796300.0, dated Dec. 21, 2017, 9 pages.

International Search Report and Written Opinion in Application No. PCT/US2012/048417, dated Nov. 21, 2012, 16 pages.

International Search Report and Written Opinion in Application No. PCT/US2015/32298, dated Aug. 25, 2015, 10 pages.

Semmelink et al., Histomorphometric Study of the Lower Urogenital Tract in Pre- and Post-Menopausal Women, Cytometry 11:700-707 (1990).

WIPO International Searching Authority, International Search Report and Written Opinion dated Jun. 24, 2015, in International Patent Application No. PCT/US2015/014500, 11 pages.

WIPO International Searching Authority, International Search Report and Written Opinion dated Nov. 26, 2012, in International Patent Application No. PCT/US2012/048419, 17 pages.

JP Office Action in Japanese Appln. No. 2017-514394, dated Feb. 25, 2019, 9 pages (with English translation).

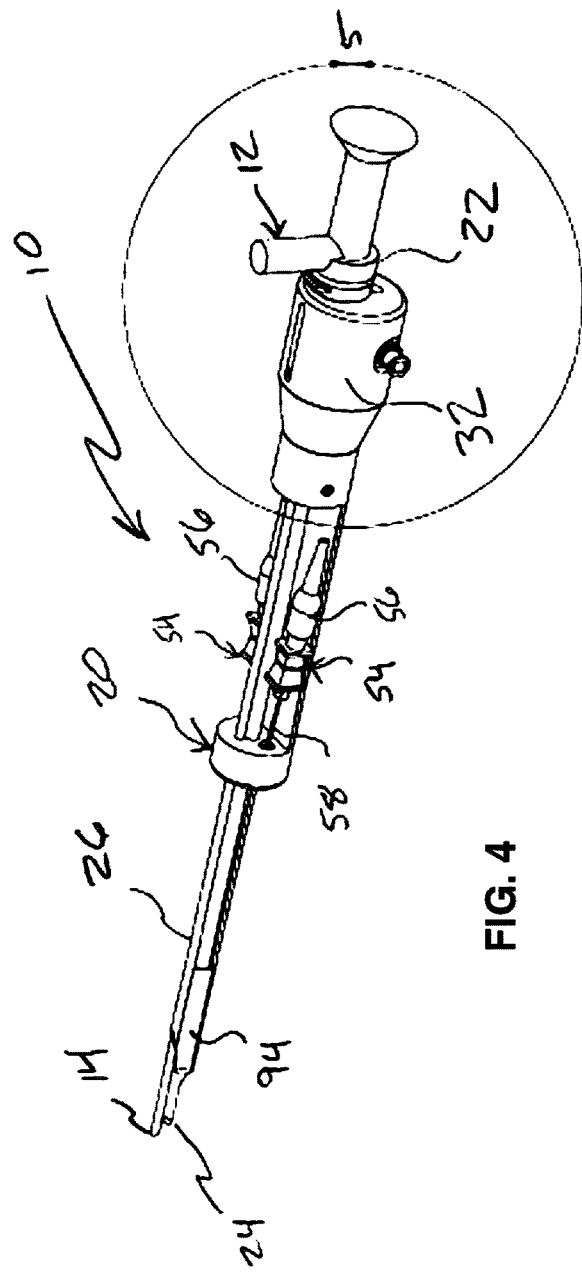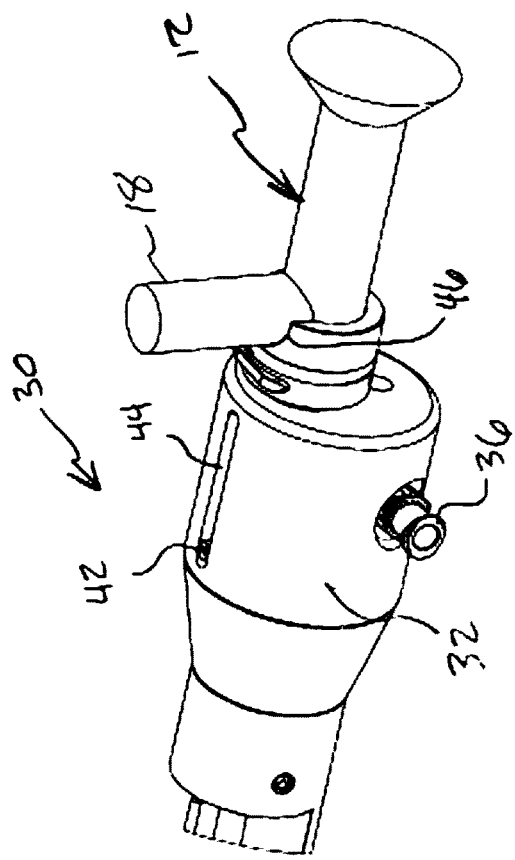
FIG. 4
FIG. 5

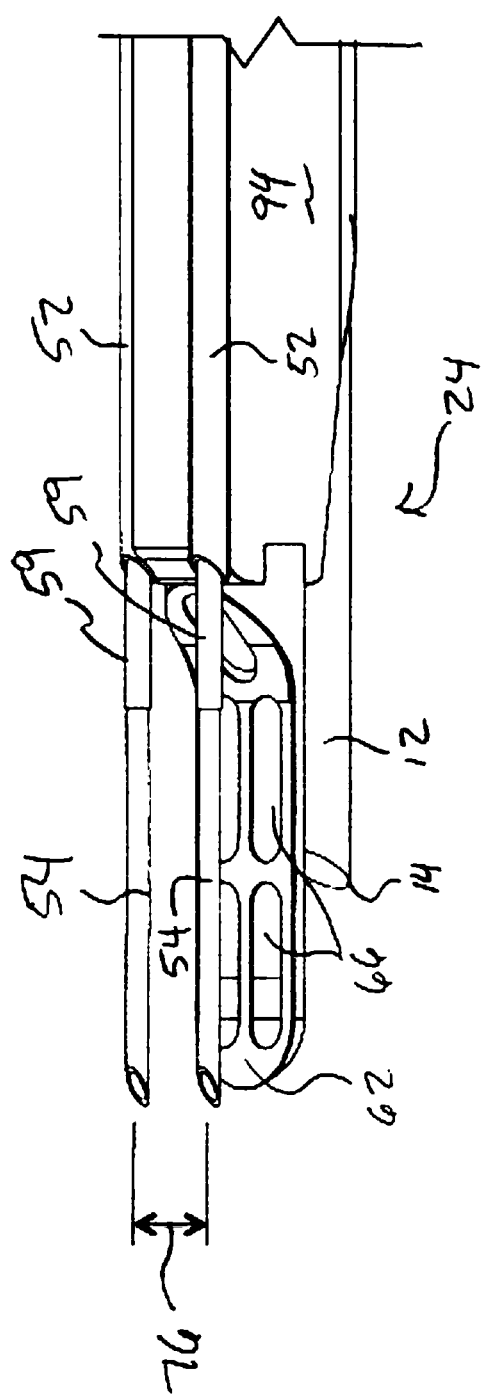
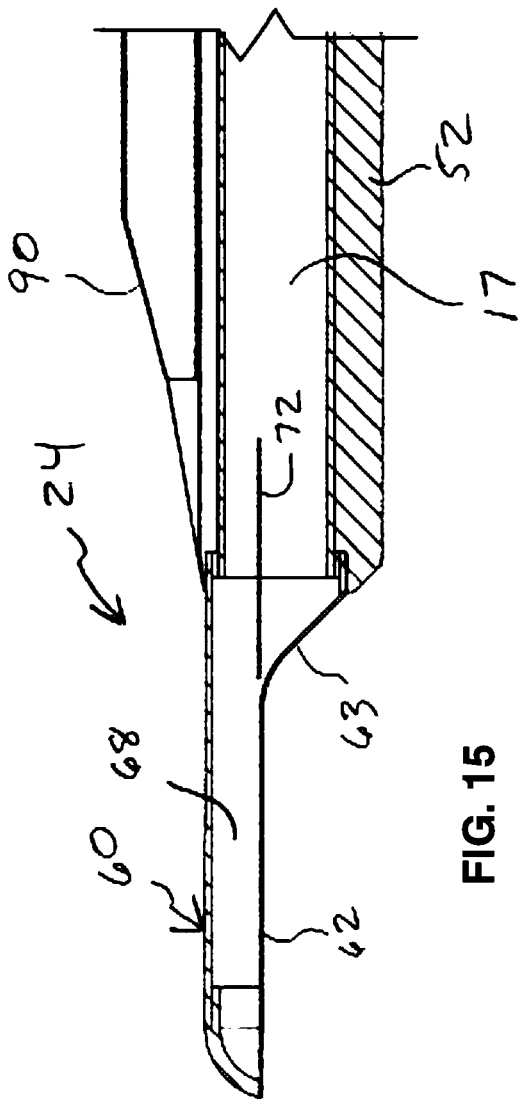
FIG. 14
FIG. 15

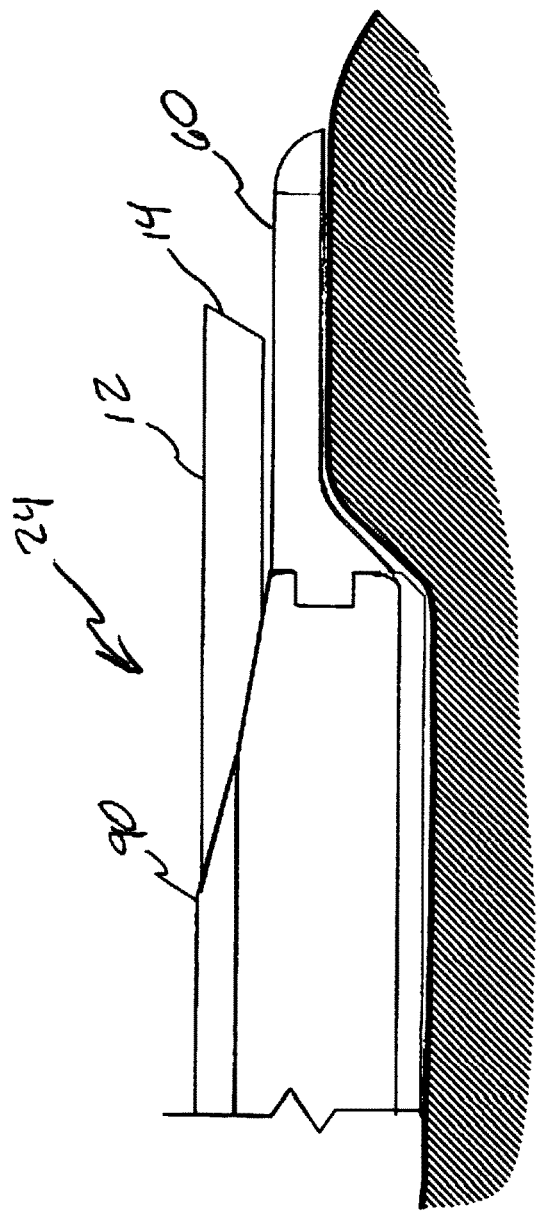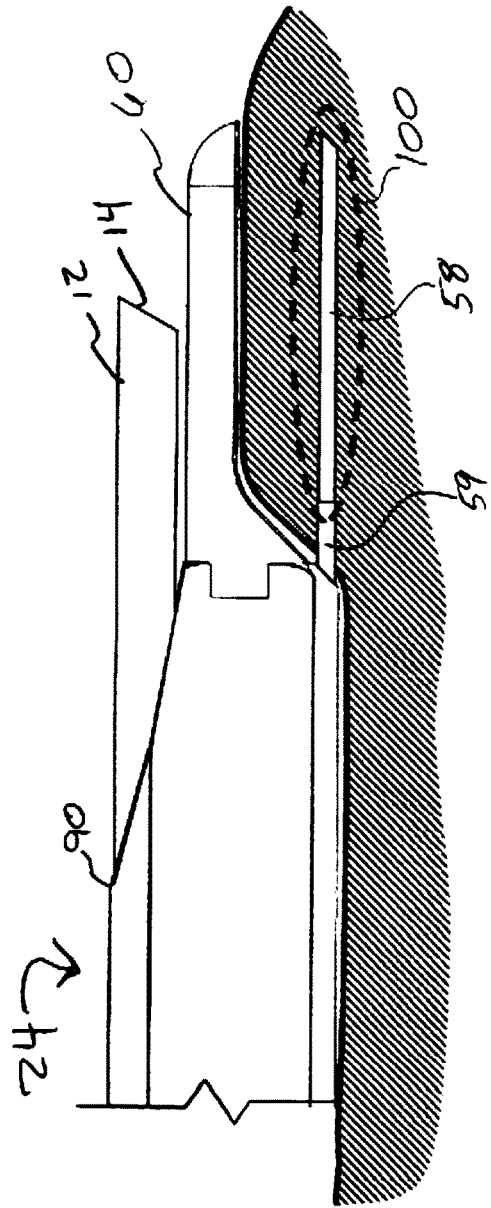

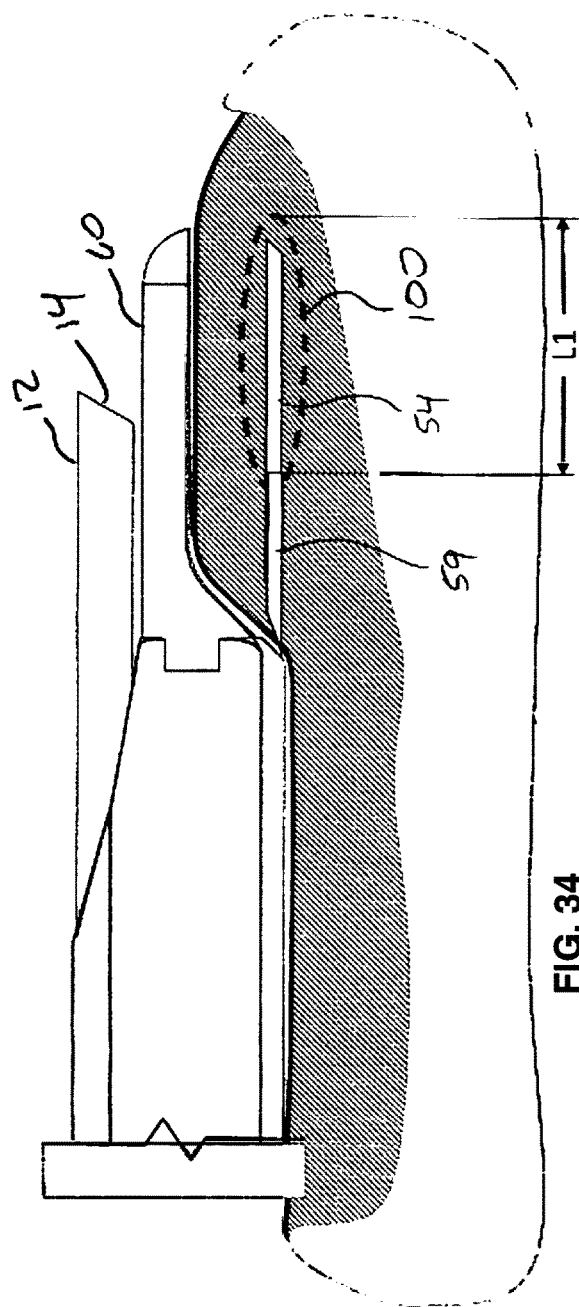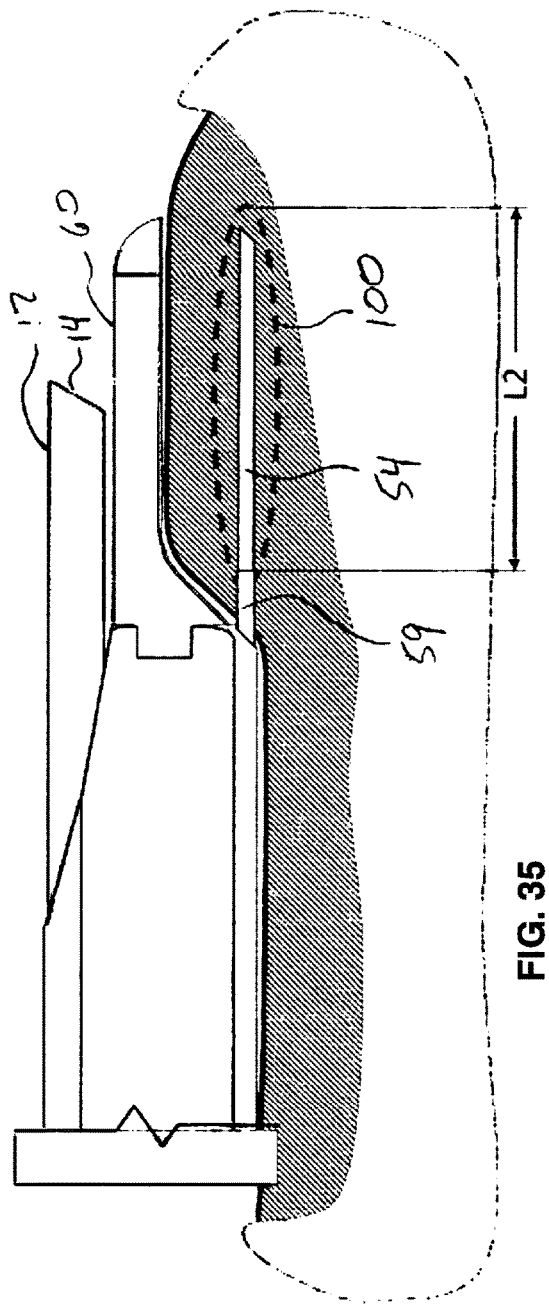
FIG. 34
FIG. 35

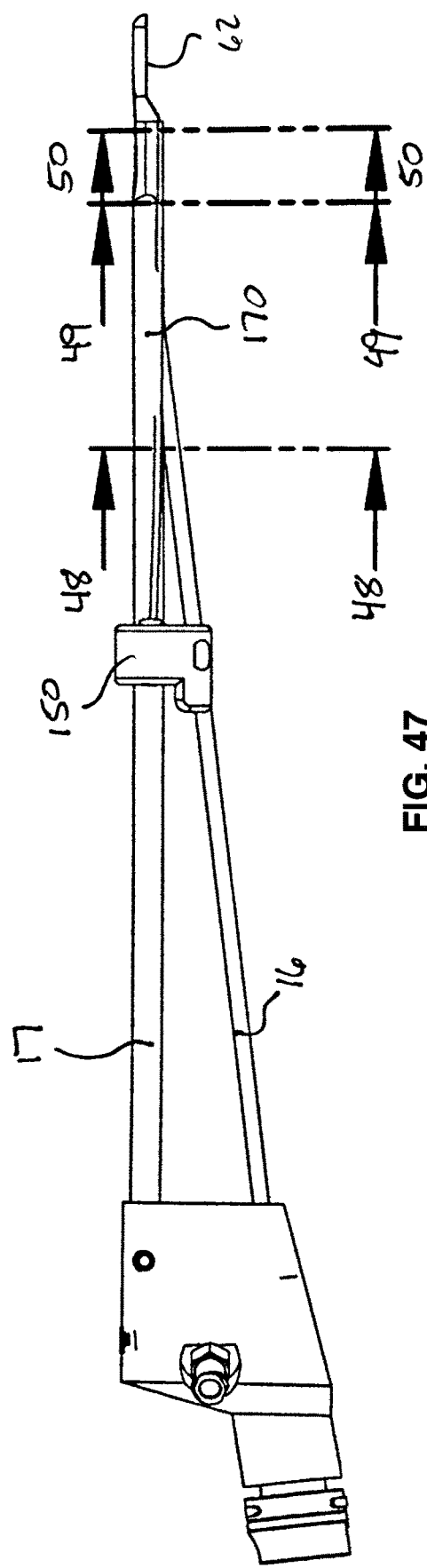
FIG. 47
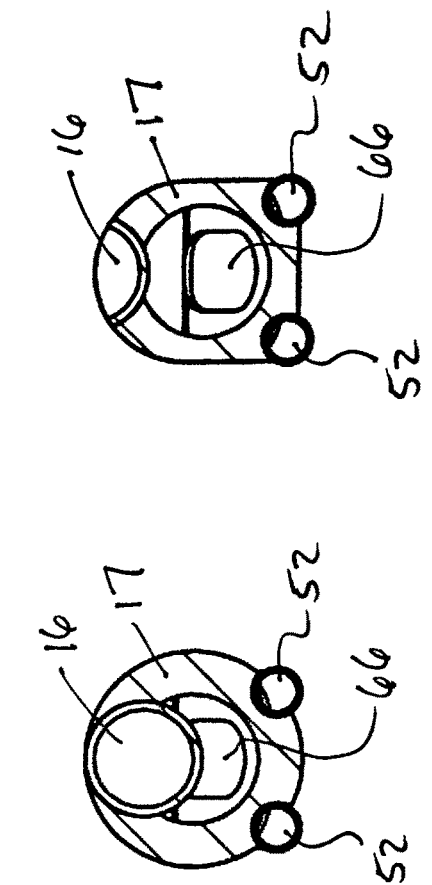
FIG. 50
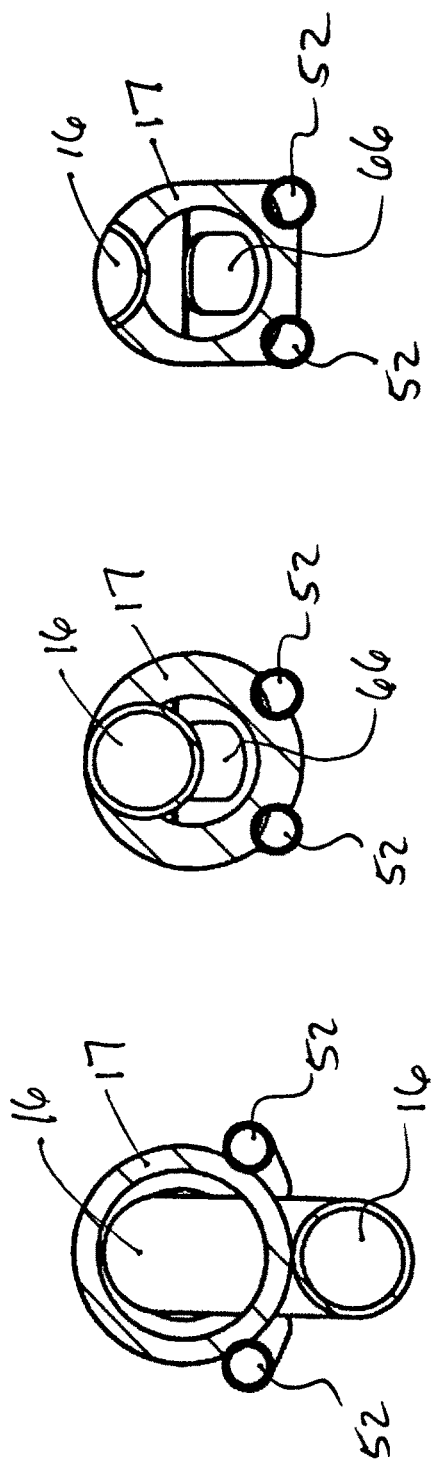
FIG. 49
FIG. 48

METHODS AND DEVICES FOR TREATING PELVIC CONDITIONS

RELATED APPLICATIONS

This application is a continuation of U.S. application Ser. No. 14/720,581, filed May 22, 2015, (now U.S. Pat. No. 10,058,381), which claims benefit of and priority to U.S. Provisional Application Ser. No. 62/002,742 filed May 23, 2014, entitled Method And Device For Treating Pelvic Conditions, which is related to U.S. patent application Ser. No. 14/030,869 filed Sep. 18, 2013, entitled Apparatus And Methods To Modulate Pelvic Nervous Tissue; U.S. patent application Ser. No. 14/285,627 filed May 22, 2014, entitled Apparatus And Methods To Modulate Pelvic Nervous Tissue; U.S. patent application Ser. No. 14/030,905 filed Sep. 18, 2013, entitled Apparatus And Methods To Modulate Bladder Function; and U.S. Provisional Patent Application No. 61/935,753 filed Feb. 4, 2014, entitled Devices And Methods For Treating Conditions Caused By Afferent Nerve Signals, all of which are hereby incorporated by reference herein in their entireties.

BACKGROUND OF THE INVENTION

Urinary incontinence (UI) is the involuntary leakage of urine. There are several types of urinary incontinence, including urge urinary incontinence (UUI) and stress urinary incontinence (SUI). Urge urinary incontinence is the involuntary loss of urine while suddenly feeling the need or urge to urinate. Stress urinary incontinence, typically affecting females, is the involuntary loss of urine resulting from increased abdominal pressure, such as generated by physical activity, exercising, coughing, sneezing, laughing, lifting, etc. Mixed incontinence combines attributes of SUI and UUI.

Overactive bladder (OAB) is the strong, sudden urge to urinate, with or without urinary incontinence, usually with frequency and nocturia. The urge associated with overactive bladder can be assessed using the subjective experience of the patient, with or without any objectively verifiable metric, condition, behavior, or phenomena.

Historically, attempts have been made to translate the subjective patient experience of overactive bladder into a verifiable clinical test. Based upon work in spinal cord injury patients, it was hypothesized that the sensation of urgency and the result of urine leakage was due to non-volitional urinary bladder detrusor muscle contractions. Consequently, there was a push to implement urodynamic testing to observe and quantify the presumed detrusor contractions. However, the results found a poor correlation (e.g., 60%) between observed detrusor overactivity and the experience of urgency, and also found that asymptomatic individuals may exhibit detrusor contractions during urodynamic testing.

Given the limitations of urodynamic testing, the diagnosis and treatment decisions for overactive bladder transitioned to being assessed wholly by the patient's subjective experience. However, the detrusor muscle and its contractions are still considered to have a major role in overactive bladder.

Bladder control is a complex combination of voluntary and involuntary neurologic control, which responds to a highly distributed set of afferent (sensory) nerves associated with the bladder. Also, there is evidence of a myogenic origin for at least a portion of bladder wall contractile activity. While there are some descriptive hallmarks of idiopathic overactive bladder (e.g., thickened wall, characteristic "patchy" denervation, changes in smooth muscle and collagen morphology, increased electrical connectivity), there is no specific anatomic cause of OAB (e.g., a lesion, defect, injury, etc.), and also it is believed that there is no commensurate remedy for the cause. Neurogenic injury (e.g., spinal cord injury) and bladder outlet obstruction (BOO) can both lead to overactive bladder due to a chronic state of bladder inflation and a "high pressure" bladder. However, resolution of an outlet obstruction fails to rectify overactive bladder symptoms in a significant fraction (e.g., 25%) of these patients.

Overactive bladder affects at least 33 million patients in the United States alone, representing 16% of the adult United States population and roughly $12 billion dollars in healthcare cost. Overactive bladder and urinary incontinence significantly affect the quality of life and the ability of patients to maintain their lifestyle, including socializing, mobility, or independence. Further, urinary incontinence is one of the most common reasons for entering long-term care facilities, such as nursing homes, and is also a significant risk factor for injury due to falls resulting from hurrying to the toilet in response to urge.

Referring to FIGS. 1-3, the anatomy of the female bladder is described to provide context for discussion of previously-known treatment modalities, and is illustrative of why a significant unmet need for improved treatment modalities remains. In particular, FIG. 1 depicts a lateral sectional of the anatomical structures of a bladder (B) and a urethra (U), while FIG. 2 depicts an anterior sectional view of the bladder and urethra. FIGS. 1-2 further illustrate a trigone (T), ureteral ostium (O) (also referred to as a ureteral orifice), detrusor muscle (D), a neck (N), an interureteric crest (C), a fundus (F), and a body (BB).

FIG. 3 depicts a cross sectional view of a wall of the bladder, including an intravesical region (IR) (also referred to as the cavity), mucous membrane (also referred to as the mucosa), lamina propria (LP), muscularis propria (MP), adventitia (A), and perivesical fat (PF). The mucous membrane lines the intravesical region (IR) of the bladder and includes a three-layered epithelium, collectively referred to as transitional cell epithelium (TCE) or urothelium, and basement membrane (BM). The three layers of the transitional cell epithelium include the basal cell layer, the intermediate cell layer, and the surface cell layer. The basal cell layer can renew the transitional cell epithelium by cell division. New cells can migrate from the basal layer to the surface cell layer, and the surface cell layer can be covered by glycosaminoglycan (GAG) layer (GL). The function of GAG layer is controversial, possibly serving as an osmotic barrier or even an antibacterial coating for transitional cell epithelium. The basement membrane is a single layer of cells that separates transitional cell epithelium from the lamina propria.

Lamina propria (also referred to as the submucosa or suburothelium) is a sheet of extracellular material that may serve as a filtration barrier or supporting structure for the mucous membrane and includes areolar connective tissue and contains blood vessels, nerves, and in some regions, glands. Muscularis propria (also referred to as the detrusor muscle or the muscle layer) may be interlaced with lamina propria and may have three layers of smooth muscle, the inner longitudinal, middle circular, and outer longitudinal muscle.

When the bladder is empty, the mucosa has numerous folds called rugae. The elasticity of rugae and transitional cell epithelium allow the bladder to expand as the bladder fills with fluid. The thickness of the mucosa and muscularis propria can range between approximately 2 to 5 mm when the bladder is full and between approximately 8 to 15 mm when the bladder is empty.

The outer surface of muscularis propria may be lined by adventitia A about the posterior and anterior surface of the bladder or by the serosa about the superior and upper lateral surfaces of the bladder. Perivesical fat (PF) can surround the bladder outside of the serosa or adventitia. In some cases, a variety of fascia layers may surround or support the organs of the pelvis. Collectively, the fascias near the urinary bladder can be referred to as perivesical fascia.

A number of therapies have been developed for treating overactive bladder, including delivery of anticholinergic drugs, bladder retraining, sacral nerve stimulation (SNS), intravesical drug infusions, surgical denervation procedures, surgeries to increase bladder volume (e.g., detrusor myomectomy, augmentation cystoplasty) and botulinum toxin (e.g., Botox®, Dysport®, etc.) injections into the bladder wall. Each of these therapies has drawbacks, as described below.

Anticholinergic drugs, used alone or in combination with traditional nonsurgical approaches, such as bladder retraining, Kegel exercises, biofeedback, etc., often is used as first-line therapy for overactive bladder; however, the mode of action is uncertain. Anticholinergic drug use was initially thought to decrease contractions of the detrusor muscle during the filling stage (e.g., detrusor muscle overactivity, unstable detrusor muscle, etc.). However, it is now believed that anticholinergic drugs may not change detrusor muscle contractility, but instead modulate afferent (e.g., cholinergic) nervous traffic to the central nervous system.

Efficacy of anticholinergic drugs is generally quite modest, as approximately 50% of patients find such therapy subjectively inadequate. A reduction of 10% to 20% in the number of micturations per day (e.g., from 11 micturations to 9 micturations) and a reduction of 50% in urinary incontinence episodes (e.g., from 2 per day to 1 per day) is typical. However, these effects are frequently inadequate to significantly improve patient quality of life (QOL). Many patients would not even notice a change of 2 micturations per day unless they are keeping a log for a formal study. The remaining urinary incontinence episodes, although slightly less in number, continue to maintain the stigma and lifestyle limitations of the disease, such as the inability to travel or to be active, social withdrawal, etc. In addition, anticholinergic drugs can have side effects, including dry mouth, constipation, altered mental status, blurred vision, etc., which may be intolerable, and in many instances outweigh the modest benefits attained. Approximately 50% of patients abandon anticholinergic therapy within 6 months.

Sacral nerve stimulation (SNS) has a higher level of efficacy (e.g., up to 80% in well-selected and screened patients), but here too the mode of action is not well understood. The clinical benefit of SNS for urinary incontinence was a serendipitous finding during clinical trials of SNS for other conditions. The SNS procedure has a number of drawbacks: it is expensive and invasive, and requires surgery for temporary lead placement to test for patient response, followed by permanent lead placement and surgical implantation of a pulse generator in patients who responded favorably to the temporary lead. Regular follow-ups also are required to titrate SNS stimulation parameters, and battery replacements are necessary at regular intervals.

A variety of surgical denervation or disruption procedures have been described in the literature, but most have showed poor efficacy or durability. The Ingelman-Sundberg procedure, first developed in the 1950s and described in Ingelman-Sundberg, A., "Partial denervation of the bladder: a new operation for the treatment of urge incontinence and similar conditions in women," Acta Obstet Gynecol Scand, 38:487, 1959, involves blunt surgical dissection of the nerves feeding the lateral aspects of the bladder near its base. The nerves are accessed from the anterior vaginal vault, with the dissection extending bilaterally to the lateral aspect of the bladder. The denervation process is accomplished somewhat blindly, using blunt dissection of the space and targeting the terminal pelvic nerve branches. Although capable of producing promising results, the procedure as originally proposed entails all of the drawbacks and expense normally associated with surgical procedures.

McGuire modified the Ingelman-Sundberg procedure in the 1990s, as described in Wan, J., et al., "Ingelman-Sundberg bladder denervation for detrusor instability," J. Urol., suppl., 145: 358A, abstract 581, 1991, to employ a more limited and central dissection within the serosal layer of the bladder, staying medial to the vaginal formices. Surgical candidates for the Modified Ingelman-Sundberg procedure can be screened to isolate likely "responders" using sub-trigonal anesthetic injections. As reported in 1996 by Cespedes in Cespedes, R. D., et al., "Modified Ingelman-Sundberg Bladder Denervation Procedure For Intractable Urge Incontinence," J. Urol., 156:1744-1747 (1996), 64% efficacy was observed at mean 15 month follow-up following the procedure. In 2002, Westney reported in Westney, O. L., et al., "Long-Term Results Of Ingelman-Sundberg Denervation Procedure For Urge Incontinence Refractory To Medical Therapy," J. Urol., 168:1044-1047 (2002), achieving similar efficacy at mean 44 month follow-up after the procedure. More recently, in 2007, Juang reported in Juang, C., et al., "Efficacy Analysis of Trans-obturator Tension-free Vaginal Tape (TVT-O) Plus Modified Ingelman-Sundberg Procedure versus TVT-O Alone in the Treatment of Mixed Urinary Incontinence: A Randomized Study," E. Urol., 51:1671-1679 (2007), using a combination of a transvaginal tape (TVT) sling (the "gold standard" surgical therapy for stress incontinence) and the Modified Ingelman-Sundberg procedure for mixed incontinence patients and showed a significant benefit for including the Modified Ingelman-Sundberg procedure, over the TVT sling alone, out to 12 months follow-up following the procedure.

Despite its clinical success, however, the Modified Ingelman-Sundberg procedure has not been widely adopted, as it is highly invasive and requires general anesthesia. Further, the terminal nerve branches are not visible to a surgeon, and thus, the dissection must be performed using approximate anatomical landmarks rather than using direct visualization of target nerve branches. Possible complications of the Modified Ingelman-Sundberg procedure include the risks associated with anesthesia, blood loss, vaginal numbness or fibrosis, adhesions, fistulas, vaginal stenosis, wound infection, or dyspareunia (pain with intercourse). Perhaps most importantly, efficacy of the Modified Ingelman-Sundberg procedure may be dependent upon surgical skill and technique.

More recently, another therapy involving injection of botulinum toxin (e.g., Botox®) into the bladder wall has been developed to address the symptoms of overactive bladder by blocking nerve traffic and causing temporary muscle paralysis following injection. During the injection procedure, which may be performed in a physician's office under local anesthesia, a cystoscope is introduced into the bladder through the urethra and a number of separate cannula injections (e.g., 20-30) are made into the bladder wall. Initially the trigone, the area of the bladder defined by the ostia of the two ureters and the urethra, was avoided due to concerns about procedural pain due to dense afferent innervation of the trigone region and the potential for vesicoureteral reflux. However, the trigone region has more recently been included, and sometimes specifically targeted to the exclusion of the dome of the bladder. Initially, botulinum toxin was assumed to act only on the efferent motor nerves (e.g., causing partial paralysis of the detrusor muscle). More recent research indicates that botulinum toxin may have an effect on afferent sensory nerves as well. U.S. Pat. No. 8,029,496 to Versi provides an example of a system for delivering such a therapeutic agent to the trigone of the bladder through the vaginal wall.

Typically, botulinum toxin injections achieve a fairly high level of efficacy (e.g., resolution of symptoms), with maximum changes in cystometric capacity peaking at 4 weeks and complete continence being achieved in about half of patients. However, botulinum toxin does carry with it the risks of systemic effects, such as flu-like symptoms, nausea, weakening of respiratory muscles, transient muscle weakness, allergic reaction, or developed sensitivity. Other adverse events associated with botulinum toxin injections include acute urinary retention (AUR), large postvoid residual volume (PVR), difficulty in urination ("straining"), and urinary tract infection (UTI). Challenges with botulinum toxin therapy include procedural skill (e.g., dexterity with cystoscope and needle), uncontrolled drug diffusion, variable needle penetration depth, and reproducibility of technique. In addition, the effects of botulinum toxin wear off with time, typically after 6-9 months, requiring repeat injections for the lifetime of the patient.

Stress urinary incontinence, typically affecting females, is an anatomic issue where the pelvic floor has been damaged and weakened, such as during childbirth. Here, front line therapies are conservative (e.g., Kegel exercises or biofeedback), and a variety of minimally invasive surgical therapies are available as second line therapies. Examples of these second line therapies include sling procedures, bladder neck suspension, transvaginal tape (TVT), etc. In each, the procedure is a day surgery performed on an outpatient basis. Success rates are high, and the procedures have been embraced by the medical community.

In addition, new therapies have been developed to treat stress urinary incontinence, such as the Renessa system offered by Novasys Medical, Inc., which is used in an office-based procedure. U.S. Pat. No. 6,692,490 to Edwards, assigned to Novasys Medical, discloses the treatment of urinary incontinence and other disorders by the application of energy and drugs.

Finally, a majority of males will develop some degree of urinary obstruction from benign prostate hyperplasia (BPH), or "enlarged prostate", over their lifetime. Since urinary obstruction is known to be a cause of overactive bladder, bladder symptoms in males are generally presumed to be secondary to the enlarged prostate. However, resolution of the urinary obstruction (e.g., by one of the many variants of transurethral treatments of the prostate) does not resolve the bladder symptoms in about a quarter of the patients. Thus, it would be desirable to offer a minimally invasive therapeutic procedure targeting these remaining patients whose symptoms remain after prostate therapy.

Further, there is a growing preference for "watchful waiting" for prostate disease, even for cases of actual prostate cancer, and many of these patients will develop symptoms of overactive bladder due to the urinary obstruction from their growing prostate. Thus, there is the potential to provide a therapy that targets the bladder symptoms prior to or instead of providing therapy targeting the prostate itself.

Males also may experience idiopathic OAB, that is OAB not secondary to an enlarged prostate or other urinary obstruction, and require a primary therapy for the OAB symptoms.

In view of the foregoing, it would be desirable to provide a minimally invasive procedure for modulating bladder function to treat or resolve overactive bladder and provides durable relief for patients suffering from these debilitating conditions.

OBJECTS AND SUMMARY OF THE INVENTION

The invention is directed to apparatus and methods configured to perform a variety of foreseen and unforeseen medical procedures and therapies. By way of non-limiting example, the apparatus and methods of the invention are suited to provide therapy to non-mucosal target tissue (or a target volume of tissue) to modulate bladder function. In an example, energy can be delivered to denervate selected portions of the bladder, such as afferent nerves located within or proximate to the trigone region of the bladder wall, to modulate bladder function and thereby provide relief for at least one of a sense of urge, incontinence, frequency, nocturia, bladder capacity, or pain.

In some examples, denervation may be accomplished by delivering thermal energy (e.g., using RF energy, microwaves, or high intensity focused ultrasound) to layers of the bladder wall beneath the mucosal layer, such as within or proximate to the trigone region. In the context of this disclosure, tissue of the female anatomy targeted for energy delivery may include one or more tissue layers of the bladder wall beneath the mucosa and extending to (but not including) the anterior vaginal wall, and are collectively referred to herein as "non-superficial tissue." Further, in the context of this disclosure, tissue of the male anatomy targeted for energy delivery may include one or more layers of the bladder wall beneath the mucosa and extending to and including the perivesical fat layer, and in the context also is referred to as "non-superficial tissue". In still other examples, thermal energy may be delivered to neural tissue, such as a pelvic nerve or its branches, within or proximate to the bladder wall to modulate nerve traffic to or from at least a portion of the bladder, thereby modulating bladder function. In accordance with some examples, suction may be used to grasp and conform a mucosal surface of the bladder wall to a first surface of a device, and energy can be delivered to non-superficial target tissue at a substantially uniform depth from the mucosal surface. Cooling also may be provided to reduce heat buildup in the mucosa. However, in some examples, a mucosal surface of the bladder wall superficial to the non-superficial target tissue can be retained substantially intact without cooling, such as by inserting an energy delivery element in the non-superficial target tissue at a substantially uniform distance from the first surface of the device and delivering energy to the non-superficial target tissue from that substantially uniform depth beneath the mucosal surface. The systems and methods described herein may be configured to deliver energy, such as thermal energy, to target tissue either from within a lumen or cavity of a body organ, for example, the bladder, or from a lumen or cavity of an adjacent organ, such as the vagina.

In the alternative, or optionally in addition, the systems and methods described herein may provide that one or more areas of the bladder be isolated or supported such as to suppress the sense of urgency. For example, surgical barriers or treatments may be used to reduce stretch of a selected region of the bladder, such as the trigone, or alternatively used as an adjunct to energy delivery to prevent nerve regrowth in a treated portion of the bladder.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 4 is a perspective view of an embodiment of a device of the invention;

FIG. 5 is a detail perspective view of the portion of the device shown in area 5 of FIG. 4;

FIG. 5a is a detail perspective view of the portion of the device shown in area 5a of FIG. 4a;

FIG. 14 is a perspective view of an embodiment of a suction head of the invention with electrode sets in an extended position;

FIG. 15 is a cutaway view of an embodiment of a suction head of the invention showing the detail of the inner suction chamber;

FIG. 20 is a depiction of a step of an embodiment of a method of the invention;

FIG. 21 is a depiction of a step of an embodiment of a method of the invention;

FIG. 34 is an elevation of a distal end of an embodiment of the invention;

FIG. 35 is an elevation of a distal end of an embodiment of the invention;

FIG. 47 is a side elevation of an embodiment of a device of the invention;

FIG. 48 is a sectional view of the embodiment of FIG. 47 taken along section lines 48-48;

FIG. 49 is a sectional view of the embodiment of FIG. 47 taken along section lines 49-49;

FIG. 50 is a sectional view of the embodiment of FIG. 47 taken along section lines 50-50;

DESCRIPTION OF EMBODIMENTS

Figure 1:
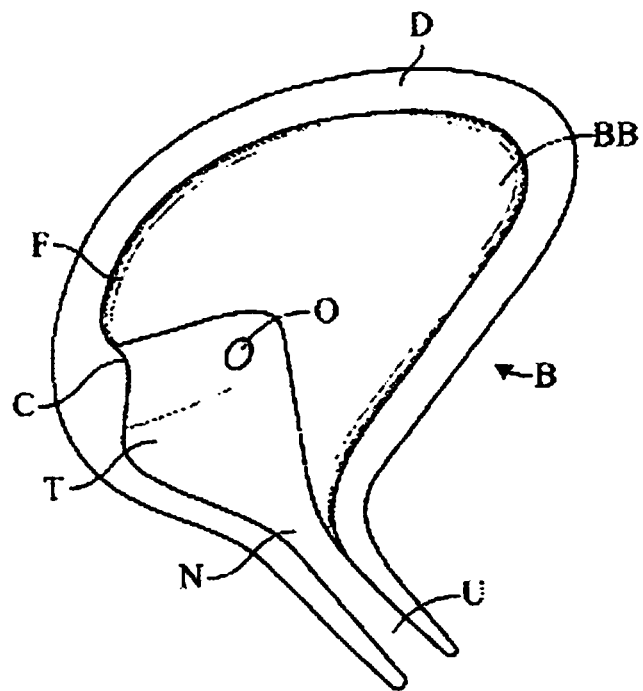
FIG. 1 is a lateral sectional depiction of the anatomy of a female bladder and urethra.
Figure 2:
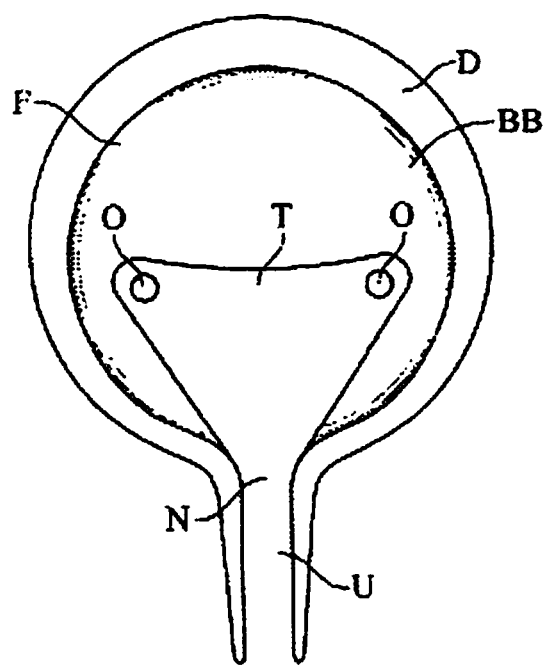
FIG. 2 is an anterior sectional depiction of a female bladder and urethra.
Figure 3:
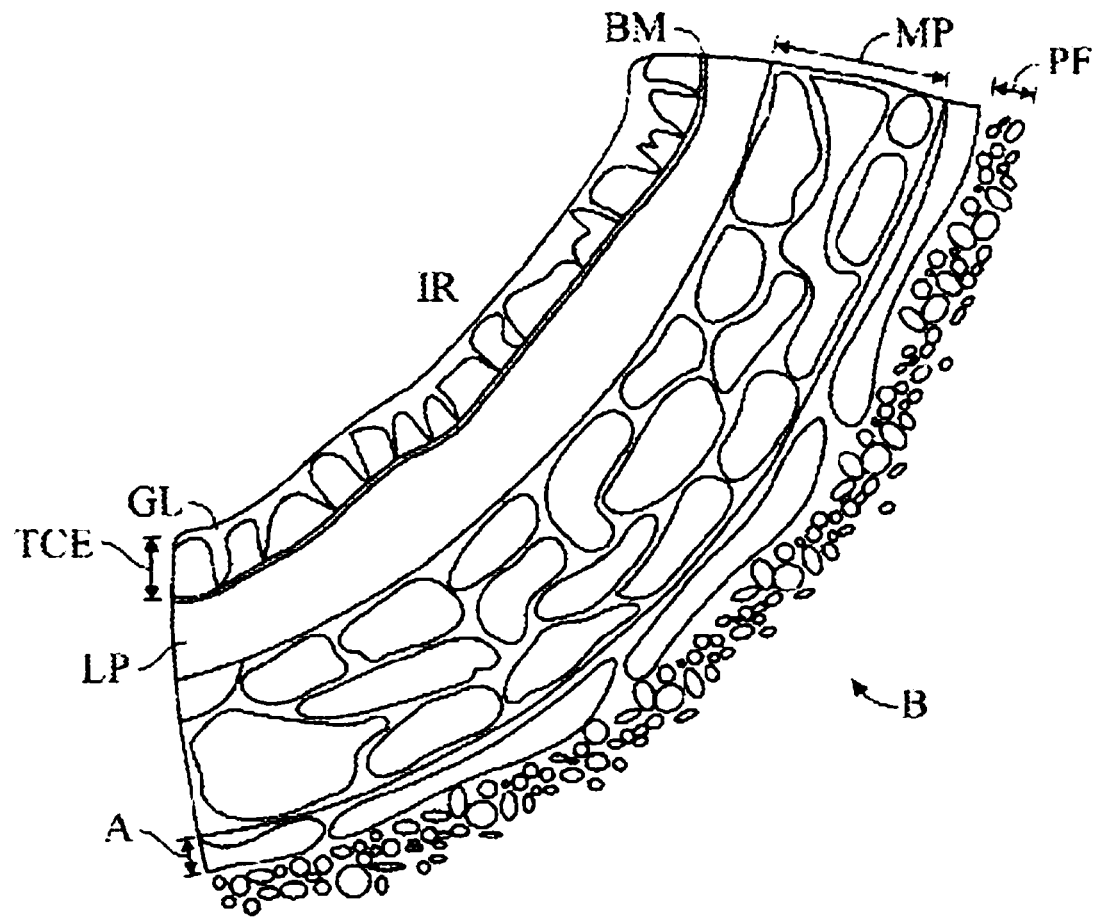
FIG. 3 is a cross sectional depiction of bladder wall tissue.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 4A:
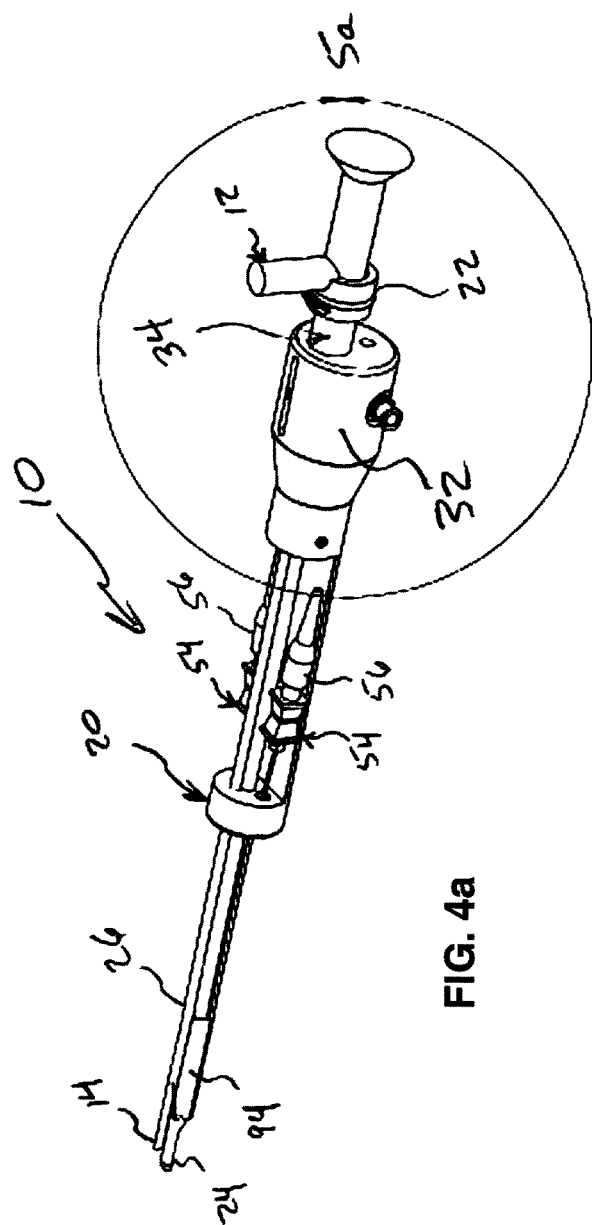
FIG. 4a is a perspective view of the device of FIG. 4 with the endoscope in a partially retracted position.

FIG. 4 illustrates an embodiment of a system 10 for treatment of body tissue, such as the bladder. Generally, the system includes a treatment device 20 and may include an endoscope 12. The treatment device 20 has a proximal end 22, a distal end 24, and an elongate shaft portion 26 between the proximal end 22 and the distal end 24.

Figure 5A:
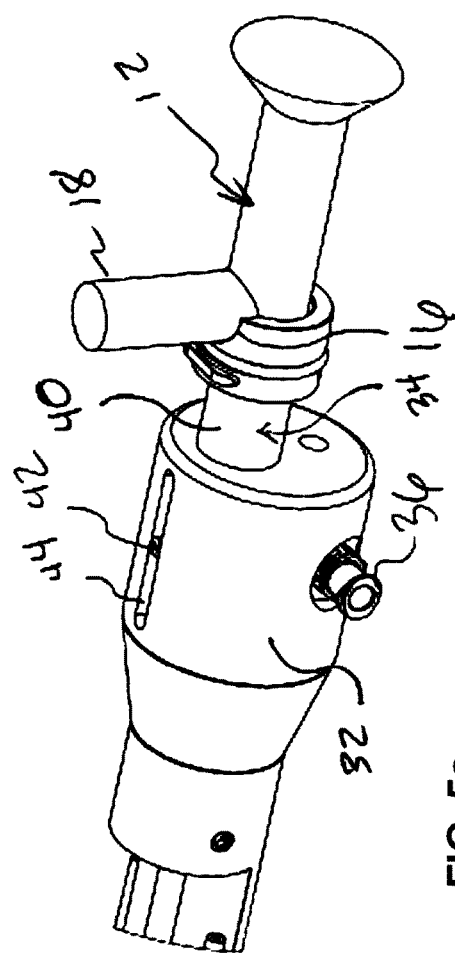

The proximal end 22 of the treatment device 20 may include a handle assembly 30, detailed in FIG. 5. The handle assembly 30 may include a body 32, a sliding mechanism 34 (FIGS. 4a and 5a), one or more suction ports 36, and at least one receiver 38 for an electrode set, described below. The handle assembly 30 generally serves to secure the endoscope position relative to the treatment device and also to provide a comfortable grip for the user. To this end, the handle assembly 30 may take on any number of ergonomic shapes. An alternative shape to that shown in the Figures is a "pistol grip" shape.

The sliding mechanism 34 functions to receive and control the longitudinal or axial placement of the endoscope 12 relative to the treatment device. The sliding mechanism 34 includes a sliding tube 40 (see FIG. 5a) that is slidingly received by the body 32 of the handle assembly 30. The sliding tube 40 includes a stop 42 that rides within a groove 44 in the body 32. The stop 42 and groove 44 define the extents of the longitudinal movement, and prevent rotation, of the sliding mechanism 34 relative to the body 32. It can be seen that the body 32 accommodates an endoscope 12 inserted into a proximal end thereof. A conventional Hopkins rod endoscope is shown, but alternative imaging devices are contemplated as well, such as endoscopes having cameras at or near their tips. The sliding tube 40 can be seen in a fully inserted position in FIGS. 4 and 5 and a partially retracted position in FIGS. 4a and 5a. A camera (not shown) may be connected to the eyepiece.

Figure 6:
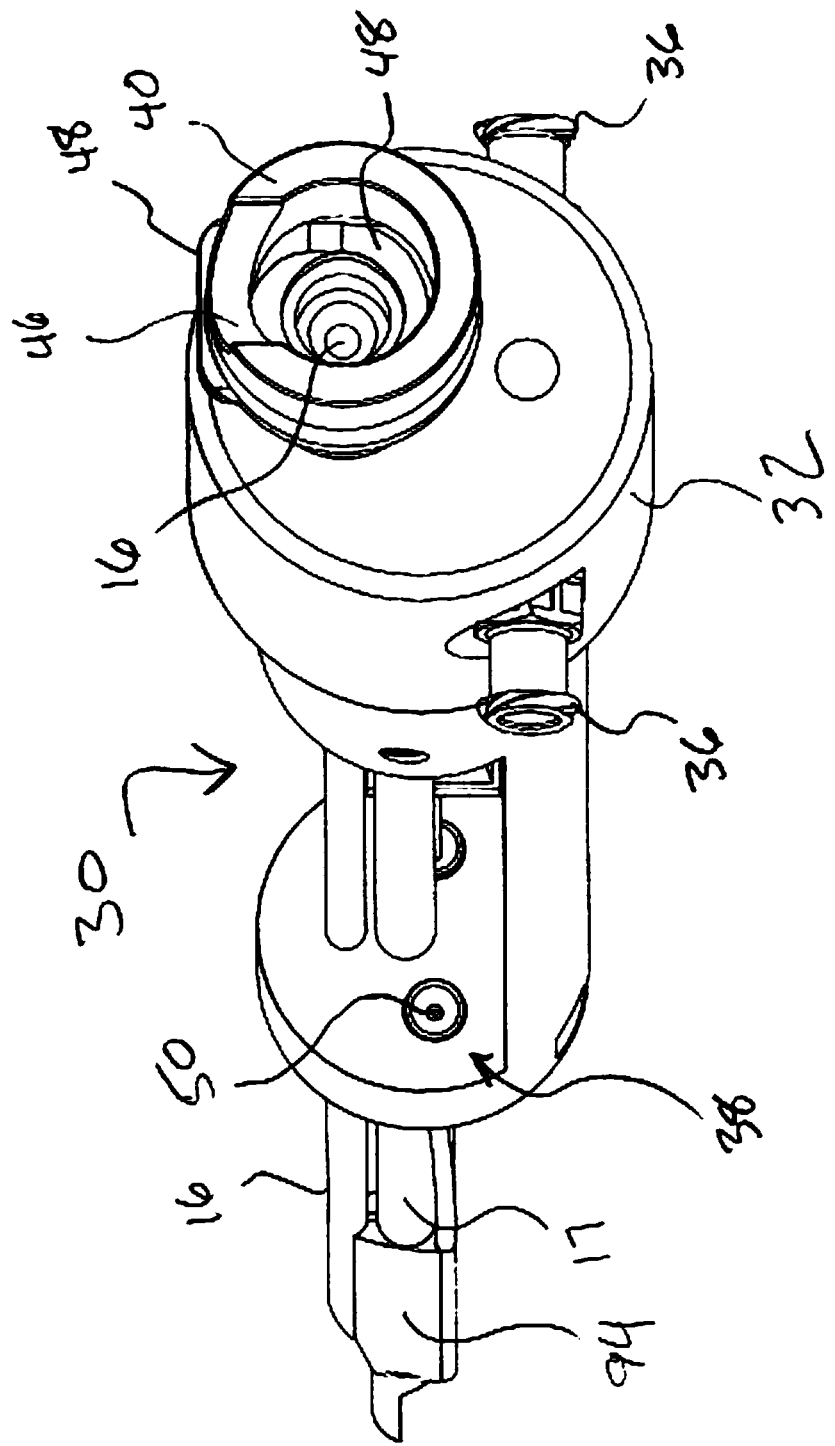
FIG. 6 is a perspective view taken from a proximal end of an embodiment of a device of the invention.

FIG. 6 shows a perspective view of the proximal end of the handle assembly 30 without the endoscope 12 inserted therein. It can be seen that the sliding tube 40 defines a proximal end of a scope channel 16 that receives the endoscope 12 and extends substantially the length of the treatment device 20. The sliding tube 40 also provides a cutout 46 for accommodating a vertical control post and/or light input port 18 of the endoscope 12. The cutout 46 establishes a radial relationship between the treatment device 20 and the endoscope 12 when the endoscope is fully inserted into the sliding tube 40 of the sliding mechanism 34. The hemispherical design of the cutout allows a user to easily retract the endoscope 12 slightly from the sliding tube 40 and rotate the scope 12 if the user desires to alter the viewing angle of the scope without rotating the treatment device 20 within the patient.

The sliding mechanism 34 also includes a locking tab 48 that extends through the sliding tube 40 and frictionally engages the endoscope 12 when depressed. The locking tab 48, when engaged with the endoscope 12, prevents longitudinal movement of the endoscope 12 relative to the sliding tube 40.

While the sliding mechanism 34 is a manual slide mechanism, other configurations are anticipated. Non-limiting examples of these other configurations include dials, rack-and-pinion mechanisms, trigger mechanisms, rocker switch configurations, worm drives, gears, stepper motors, and the like.

Below the scope channel 16, the body 32 of the handle assembly includes at least one suction port 36. The embodiment shown in the Figures includes two suction ports 36. These suction ports 36 are in fluid communication with a suction channel 17 that extends the length of the treatment device 20. The suction ports 36 are shown with standard Luer-Lok fittings but this is shown by way of example only and is not intended to be limiting.

Additionally, these suction ports 36 may be used for irrigation or infusion purposes. Flow control valves (not shown), such as stopcocks may be used to connect suction and/or aspiration sources to the ports 36. One or more of the ports 36 may also act as a vent to the atmosphere. It is also envisioned that one or more of the fittings may be permanently or episodically connected to a syringe, which may be used to instill or extract volumes of fluid into or out of the anatomic structure in which the device is used.

The body 32 of the handle assembly 30 also may define one or more receiver 38 for an electrode set. The embodiment shown in the figures includes a receiver 38 that accommodates two electrode sets 54, one on either side of the scope channel 16 and the suction channel 17. The receiver 38 is sized and shaped to house the proximal ends of the electrode sets 54 and provides cannula ports 50 that lead to cannula channels 52. The cannula ports 50 are shown as being funneled in order to facilitate easy cannula insertion.

The electrode sets 54 are best shown in FIGS. 4 and 7-9. The electrode sets 54 generally include an electrode 56 and a cannula 58 extending distally therefrom. Connecting wires connecting the electrodes 56 to a power source are to be understood but not shown. The electrode 56 extends through and energizes the cannula at the tip. An all-in-one electrode set, in which the conductive end of the electrode is not contained within a cannula is also contemplated. For purposes of clarity herein, the electrode 56 is considered that portion of the electrode set that is connected to a power supply and provides the circuitry for energizing the cannula. The cannula 58 is the energized portion of the electrode set that transfers energy into the patient.

The electrode sets 54 and corresponding cannula channels 52 are sized such that, when the electrode sets are fully inserted into the cannula channels 52 so that the hubs of the cannulas 58 abut against the receiver 38, the distal ends of the cannulas 58 extend a desired amount past the distal ends 80 of the cannula channels. FIG. 14 shows the distal end of the device with the cannulas 58 fully inserted. FIG. 14 also shows insulation 59 surrounding all but the ends of the cannulas 58, thereby limiting the effective treatment portion of the cannulas 58 to the distal ends of the cannulas.

The electrode sets 54, once placed in the channels 52 and receiver 38, are movable between a retracted position and an inserted position. The inserted position as described above, is achieved when the electrode sets 54 are fully inserted into the channels 52 so that the hubs of the cannulas 58 abut against the receiver 38. The retracted position is achieved when the electrodes 56 are pulled proximally as shown in FIG. 4. In the retracted position, the distal ends of the cannulas 58 are contained within the cannula channels 52 and do not extend out of the cannula channel ends 80. The receiver 68 is sized to accommodate the electrodes 56 even when the electrode sets 54 are in the retracted position.

It is to be understood that any suitable electrode may be utilized with treatment device. While a preferred type is one that has a needle-shaped end or where an electrode resides within a cannula, such as that manufactured by Stryker, Cosman, Neurotherm, other electrodes are also contemplated, such as electrodes that are "one piece" and capable of directly penetrating tissue without an external cannula. It is also preferable to use an electrode of the type that has a temperature measurement element at its tip, such as an embedded thermocouple or thermistor. The types manufactured by Stryker, Cosman, Neurotherm include this feature.

It is anticipated that embodiments of the system 10 may be provided wherein the electrodes and cannulas are integral to the treatment device itself rather than using separate components that are assembled by the operator. Further, it is anticipated that the cannula advancement, shown here as manual axial movement of each cannula separately, may be alternatively configured to include coupling of the cannulas for simultaneous advancement and mechanisms to advance the cannulas.

The embodiment depicted in FIG. 4 does not include a mechanism for advancing the cannulas 58 from the retracted to the advanced positions, as it is envisioned that this may be done manually. However, such mechanisms are envisioned and could be provided for faster easier operation of the device. Examples of such mechanisms include trigger mechanisms or rotational helically threaded mechanisms to advance, and possibly also retract the cannulas. Also anticipated are "spring loaded" mechanisms whereby stored energy, preferably in the form of a compacted spring, is released to drive the cannulas into the tissue.

It is envisioned that one or two electrode sets may be used to ablate tissue. If two electrode sets are utilized, as shown in the figures, a bi-polar current may be applied, which concentrates current in relatively planar space between the exposed portions of the cannulas.

Additionally, if two electrode sets are used in a bi-polar configuration (or more than two cannulas, but multiplexed such that they are energized in pairs) wherein the cannulas are parallel to each other along their uninsulated portion, the result is an energy deposition region which is uniform in cross section along the length of the uninsulated length. i.e., a treatment that is uniform in thickness and width along the length of the cannula.

Figure 7:
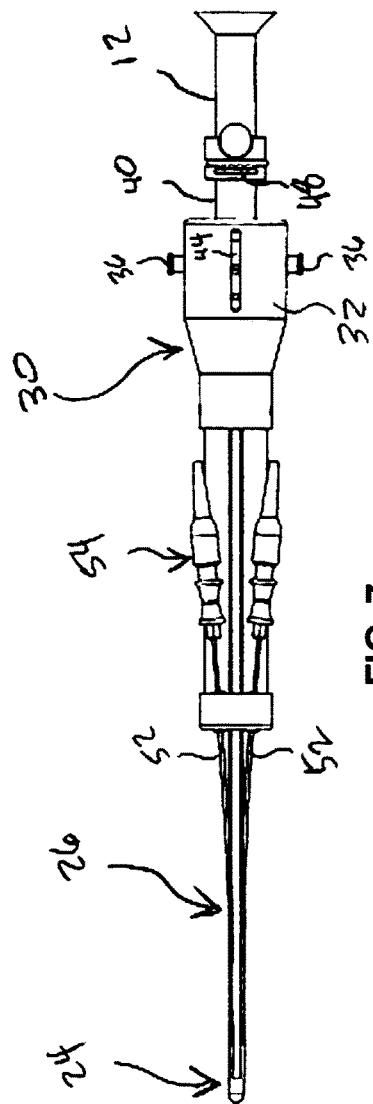
FIG. 7 is a plan view of an embodiment of a device of the invention.
Figure 8:
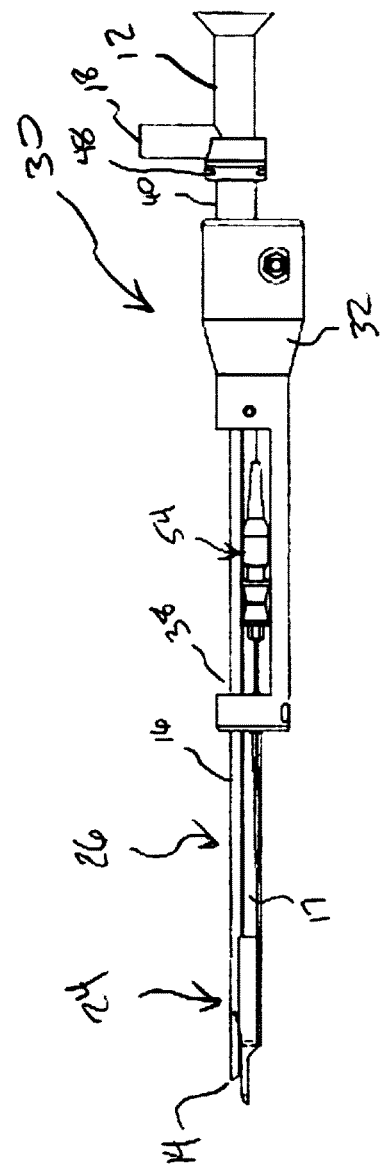
FIG. 8 is an elevation view of an embodiment of a device of the invention.
Figure 9:
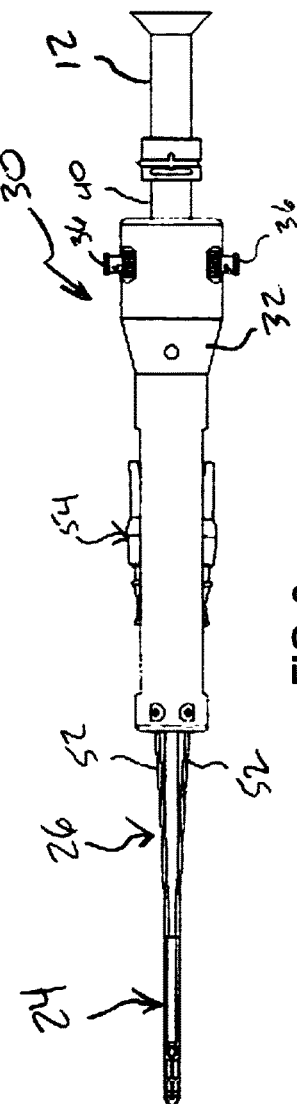
FIG. 9 is a bottom view of an embodiment of a device of the invention.

Referring to FIGS. 7-9, distal of the handle assembly 30 is the shaft portion 26. The shaft portion 26 is generally made up of the scope channel 16, the suction channel 17 and the cannula channels 52. The cannula channels 52 may be curved, as shown, to provide a smaller device profile at the distal aspect. The shaft portion 26 is shaped and sized for insertion into a female urethra and may be relatively rigid, considering that the female urethra is relatively short and straight, compared to the male anatomy. An embodiment of the device designed for use with the male anatomy is substantially similar to the embodiments shown in the figures except that it may utilize a flexible shaft portion and may include a steering mechanism.

The treatment device 20 has a distal end 24, several embodiments of which are detailed in FIGS. 10-15. The distal end 24 generally includes a suction head 60, distal cannula channel ends 80, an endoscope channel distal end 90, and a tube holder 94.

The suction head 60 includes a flat face 62 and heel portion 63 with one or more angled or curved faces 64. These faces 62 and 64 define at least one suction aperture 66. The embodiments shown in the Figures include a plurality of suction apertures 66 in various shapes and arrangements, each of which is described in more detail below. The suction apertures 66 lead to a suction chamber 68 that is in fluid communication with the suction channel 17.

The suction head 60 may include a rounded, atraumatic distal end. The flat face 62 may extend from the distal end of the suction head 60 to the heel portion 63. The shape of the suction head 60 is designed to seal itself to soft tissue when a suction is applied to the suction chamber 68. The flat face 62 establishes a seal with the soft tissue being targeted while the faces 64 of the heel portion 63 provide a gentle transition to the cannula channel ends 80.

Figure 16:
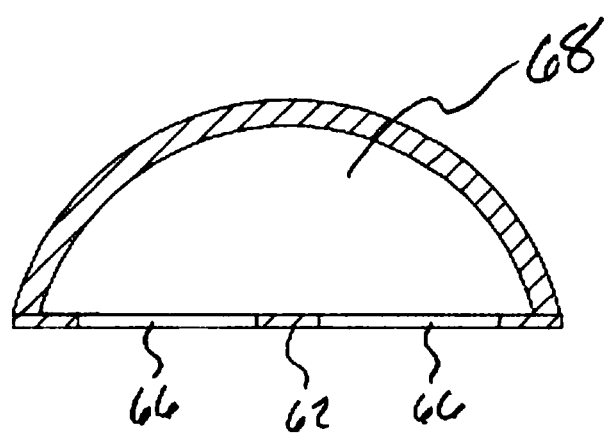
FIG. 16 is an axial cross sectional view of an embodiment of a suction head of the invention.

FIG. 16 shows an axial cross section of the suction head 60 taken at a mid-point of the flat face 62. It is shown that the shape of the suction head 60 may be generally semi-circular. It may be formed from a portion of tube cut away, with a relatively flat face attached thereto. Apertures 66 may be cut or otherwise formed in the face to form openings into the interior suction chamber 68 of the suction head 60.

Figure 11:
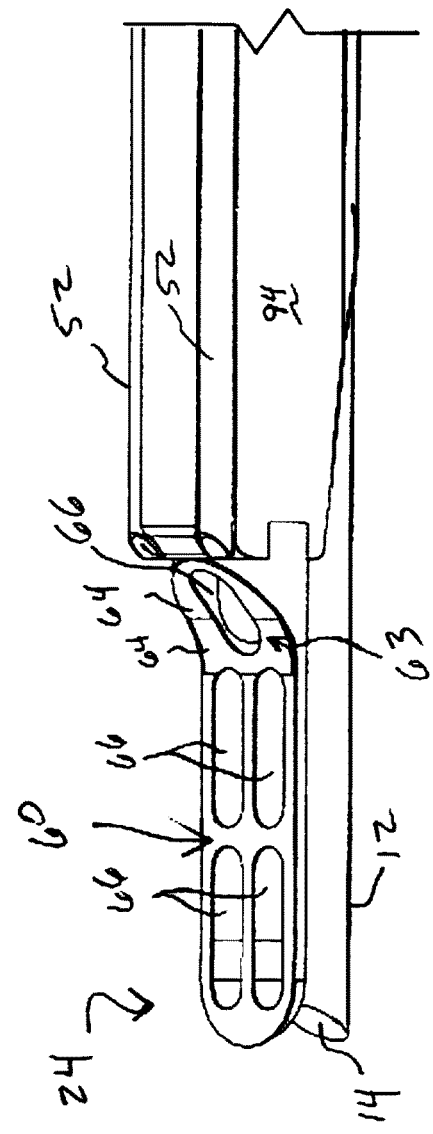
FIG. 11 is a perspective view of an embodiment of a suction head of the invention.
Figure 12:
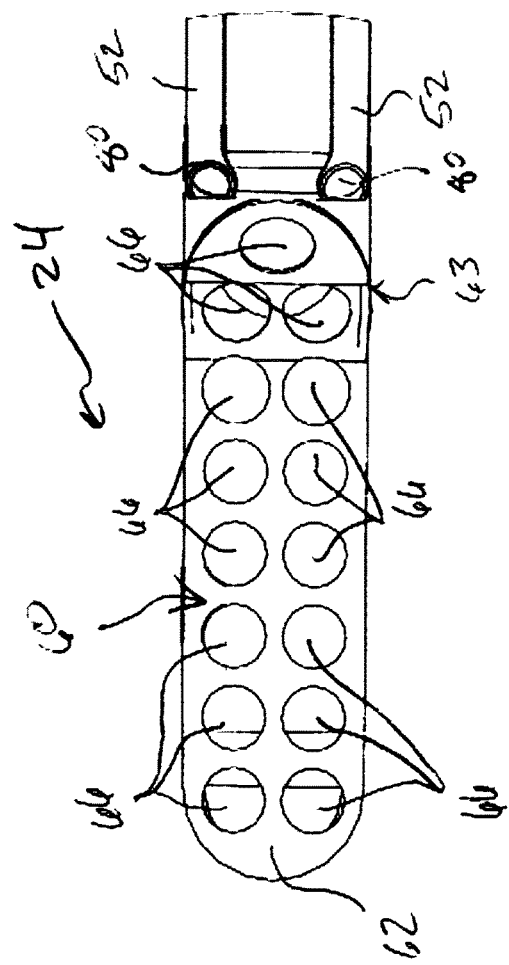
FIG. 12 is a plan view of an embodiment of a suction head of the invention.
Figure 13:
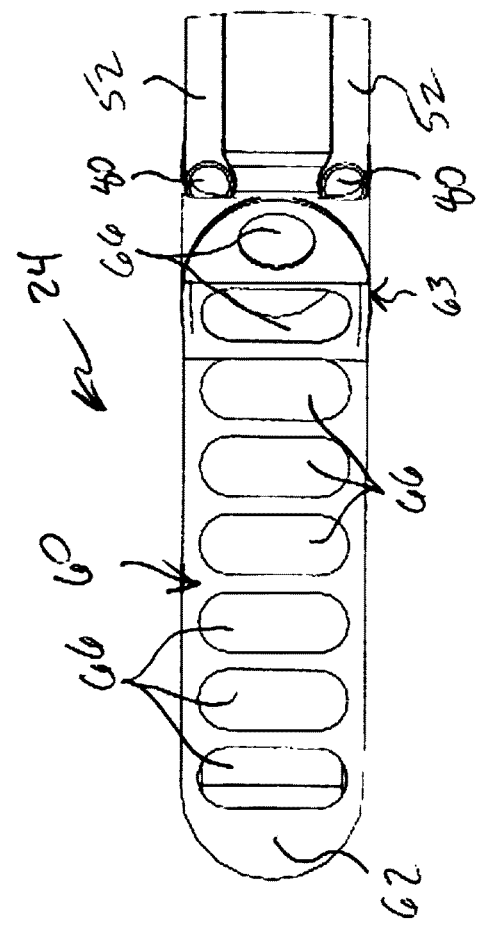
FIG. 13 is a plan view of an embodiment of a suction head of the invention.

As stated above, the suction apertures 66 may be configured with various sizes, shapes and arrangements. By way of example only, FIG. 11 shows an embodiment that uses four longitudinally-elongated apertures 66 in a 2×2 arrangement in the flat face 62 and a single aperture 66 in the angled face 64. FIG. 12 shows an embodiment whereby the flat face 62 has 12 circular apertures 66 in a 2×6 arrangement and a heel portion 63 has two angled faces 64, one with two apertures 66 and one with a single aperture 66. FIG. 13 shows an embodiment whereby the flat face 62 has six transversely elongate apertures 66 and a heel portion 63 with a first angled face 64 having a similar transversely elongate aperture 66 and another angled face 64 with a single circular aperture 66.

Alternatively, or additionally, the apertures 66 may be square or any other suitable shape, and combinations of various sizes and shapes are further contemplated both for the face and for the heel portion 63. Screen material (not shown) covering one or more of the windows is also contemplated. While the suction face shown in the figures is relatively planar, it is further contemplated that the face may have additional features, such as a raised rim at or near the edge, or along one or more of the windows, or recessed features such as plugs that limit tissue incursion into the suction windows.

As stated above, the apertures 66 lead into the suction chamber 68, which is in fluid communication with the suction channel 17. The suction chamber 68 is best shown in FIG. 15. In this embodiment, the suction chamber 68 includes a baffle 72. The baffle 72 provides a barrier between the portion of the suction chamber 68 directly adjacent the flat face 62 of the suction head 60 and the portion of the suction chamber adjacent, or proximal of, the heel portion 63. When suction is applied to tissue, a balance is sought between the strength of the vacuum being applied and the thickness and resiliency of the tissue. If the tissue is too flexible for a given vacuum level, it may be that the tissue is drawn into the suction chamber 68. The baffle 72 ensures that the suction chamber 68 is not completely blocked by tissue. Thus, even if tissue is drawn into the heel portion 63, a path exists on the opposite side of the baffle 72 for a vacuum to be established adjacent the flat face 62.

The heel portion 63 serves at least two functions. A first function of the heel portion 63 is to hold the tissue being engaged by the apertures 66 in the angled faces 64 and prevent that tissue from being pushed away from the suction head 60 when the electrode sets are being advanced into the tissue. The orientation of the angled faces 64 assists in resisting longitudinal movement by the tissue as a result of the advancement of the electrode sets.

As discussed above, a second function of the heel portion 63 is to provide a transition between the flat face 62 and the cannula channel ends 80. The vertical separation 74 (FIG. 10) between the flat face 62 and the cannula channels 52 helps define the depth at which the electrode sets/cannulas will penetrate and treat the targeted tissue. This vertical separation 74 allows the electrode sets to engage the targeted tissue layer below the surface while avoiding or minimizing treatment of the surface layer of the bladder interior.

More specifically, for bladder applications such as ablation of portions of the trigone region of the bladder for treatment of overactive bladder, an example of a desired spacing is between 0.5 and 5.0 mm and preferably between 1.0 and 4.0 mm. In this manner, it is believed that the thermal treatment of the submucosal tissue is concentrated at around 0.0 to 7.0 mm depth from the bladder surface, which is where disruption of the afferent nerves is believed to be effective, while minimizing thermal effects at the surface of the bladder. Greater or lesser spacing is also contemplated. The horizontal spacing 76 between the cannulas has an impact on the width of the thermal treatment zone. A preferred spacing (shown in FIG. 14) is from 3 to 5 mm.

Figure 10:
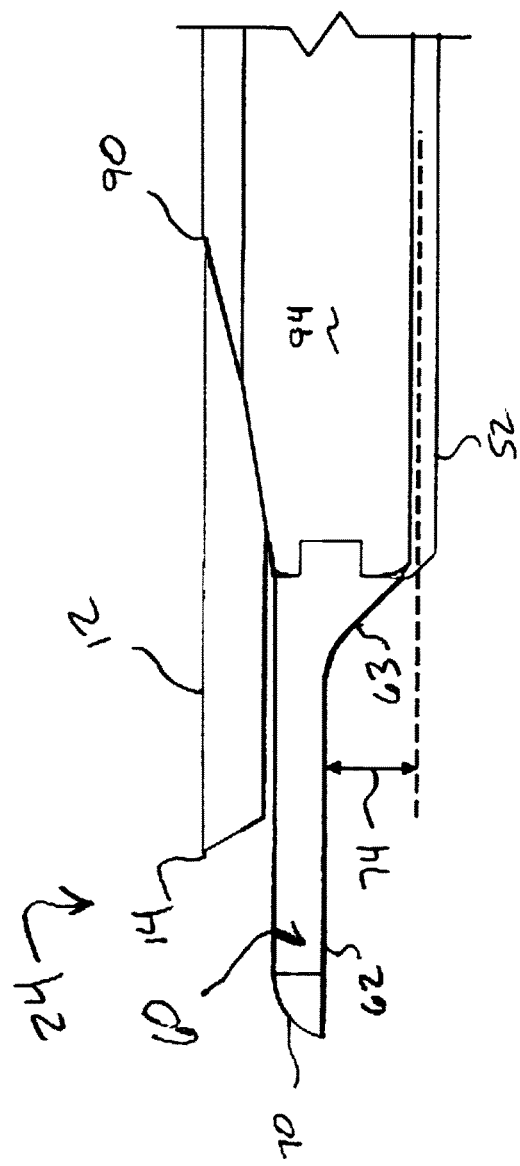
FIG. 10 is an elevation of an embodiment of a suction head of the invention.

FIG. 10 illustrates a configuration where the axis of the cannula and the suction head are parallel (i.e., the cannula is at a uniform distance from the flat face 62 along the entire length of the face 62). While this is a preferred embodiment, it is also anticipated that certain non-zero angles between the paddle and cannula may offer certain benefits. For example, a non-zero angle could be chosen to bias the distal portion of the cannulas (and thus the therapy) to be at a different distance, either to bias the therapy to a different, preferential, depth, or to correct for differences in tissue properties or cannula tracking through the tissue.

FIGS. 10 and 15 show that the device distal end 24 also includes the endoscope channel end 90. The endoscope channel end 90 is angled such that, when the scope is retracted, the channel end presents an atraumatic profile.

FIG. 10 shows the end of the endoscope 12 in a partially advanced position such that it protrudes out of the endoscope channel end 90. (By way of comparison, FIG. 11 shows the scope 12 in a fully advanced position). In this partially advanced position, the scope 12 has a view of the suction head 60 as well as the tissue ahead of the suction head 60.

It may be desirable for the endoscope to be spaced a distance radially from the surface of the suction head 60. Such spacing allows for the endoscope image to be less "blocked" by the presence of the suction head, facilitating more precise placement of the suction head against the desired body tissue. For bladder applications, and in the case where the endoscope has a 25-35 degree viewing angle, and is in the diameter range of about 2.5 to 3 mm in diameter, and where the suction head is in the range of about 4.5 to 5.5 mm in width, the spacing is preferably about 0.25 to 0.75 mm, although more or less is also contemplated. Greater spacing, while further minimizing the amount of blocked view of the suction head 60, also forces the overall device diameter to become larger, which is undesirable in applications where overall device profile is desired to be smaller, such as the bladder, where the device is inserted into the urethra.

The device distal end 24 also may include a tube holder 94. The tube holder 94 is a housing that may be used to connect the various tubes/channels of the treatment device 20, as shown in FIG. 10. The tube holder 94 secures the endoscope tube 16, the suction tube 17, and the electrode tubes 52. This arrangement of the tubes, with a non-circular outer shape, allows the distal portion of the treatment device to contain all the tubular elements in a desired arrangement, while minimizing the overall periphery dimension, thus facilitating placement of the device into anatomy such as the urethra to access the bladder.

The aforementioned embodiments, and those additional embodiment described below, may be useful to perform various procedures and methods of the invention. For example, the embodiments may be used to treat bladder conditions such as Over-Active Bladder (OAB).

Figure 18:
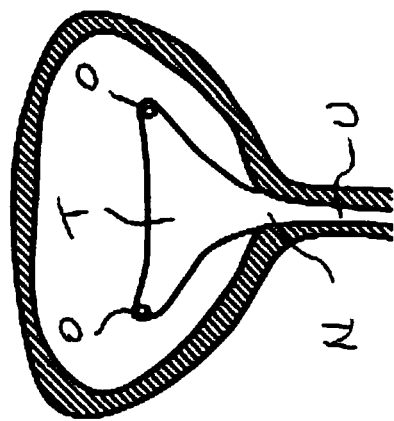
FIG. 18 is an anterior sectional depiction of a bottom portion of a female bladder.
Figure 17:
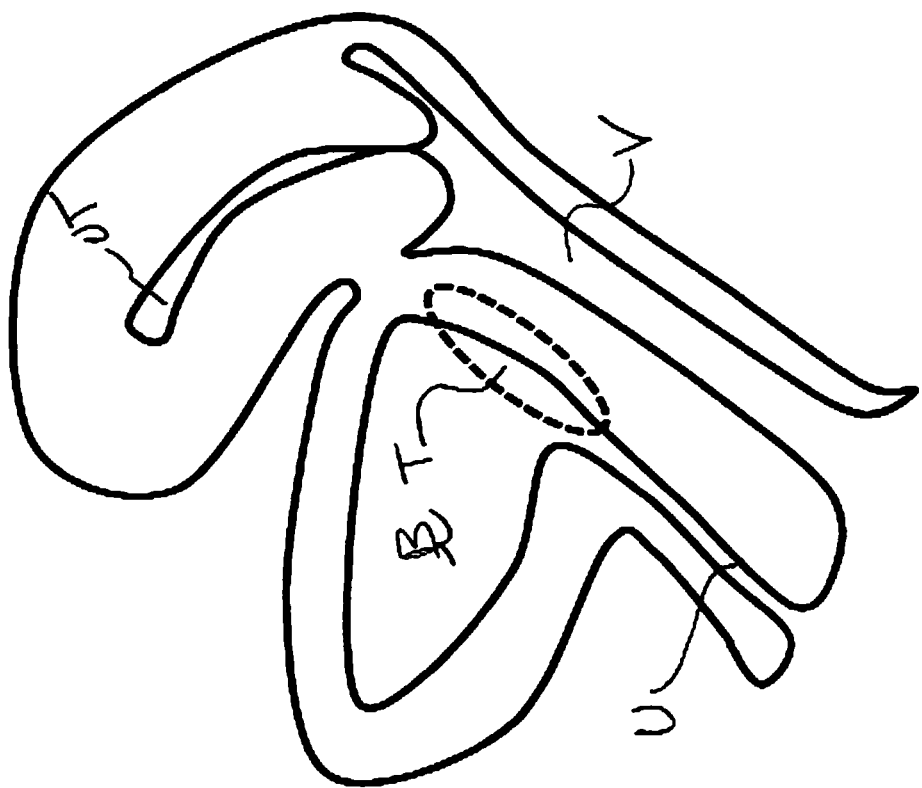
FIG. 17 is a depiction of a side view of an area of a female bladder targeted during an example of a method of the invention.

In this regard, FIG. 17 is a side view showing the female anatomy, including the bladder B, the uterus UT, the vagina V, and the urethra U. The trigone region T is shown in the dashed region. FIG. 18 shows an angled frontal-axial sectional view of the bottom portion of the bladder B, including the trigone region T, the ureteric ostia O, the bladder neck N, and the urethra U. While use of one of the device embodiments of the present invention is described in connection with the female anatomy, the same or similar device is contemplated for use in the male anatomy as well. Some design alterations may be used, including lengthening portions of the treatment device, and/or making the device more flexible and/or deflectable.

Figure 19:
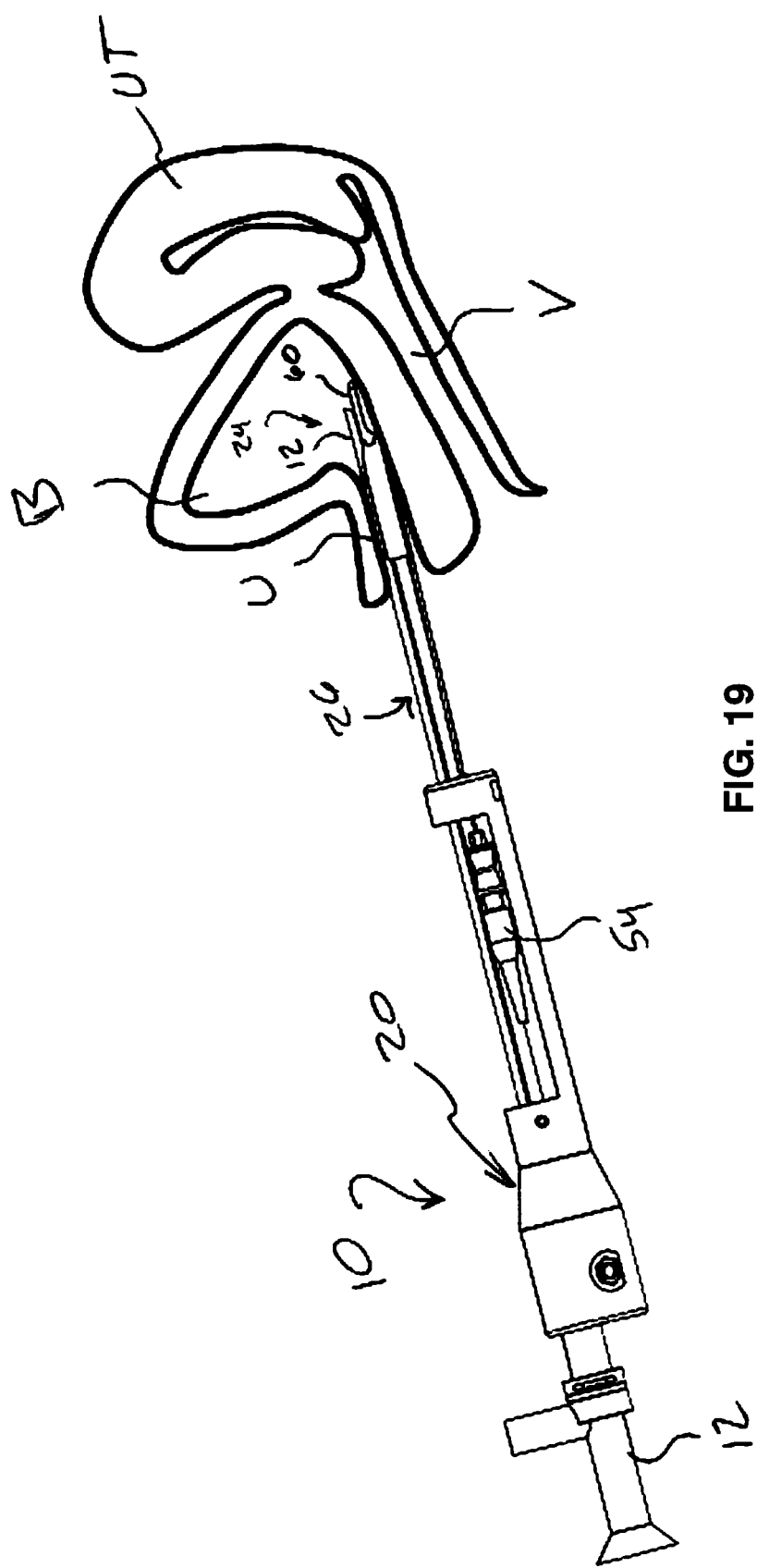
FIG. 19 is a depiction of an embodiment of a device of the invention being inserted into a female bladder.

Treatment device 20 may be first inserted into the urethra and into the bladder, as shown in FIG. 19 (note that for purposes of simplicity, the camera and light cable are not shown connected to the endoscope 12, nor are the suction and infusion tubes or devices shown hooked up the ports). The endoscope 12 is preferably positioned nearer the distal end of the suction head during this step. The treatment device 20 and endoscope 12 may be inserted directly into the urethra, or may be placed through a prior positioned tubular sheath (not shown).

If the target tissue is the trigonal region of the bladder, it may be desirable to initially identify one of the ureteric ostia. The ostium may be marked ahead of time by placement of a guide wire, a suture loop, or may be just visualized during the placement of the treatment device, with care to avoid placement of the treatment device at or too close the ostium. In a preferred method, the tip of the suction head is placed just medial to the uretic ostium. In another embodiment, the suction head is placed just inferior to the uretic ostium. In both cases, the ureter itself is protected since as the ureter travels lateral and superior away from the visible ostia, placements medial and inferior avoid the obscured ureter.

The suction head 60 is placed onto the surface of the bladder tissue and the suction is activated, causing the surface tissue of the bladder to come into intimate contact with the face of the suction head, as shown in FIG. 20. Use of movement stabilization devices connected to the handle are contemplated, for example, it may be beneficial to stabilize the position of the treatment device after the suction is activated and the tissue engaged with the suction head.

Though not shown, the tissue may actually protrude within the apertures on the suction head 60. The suction engages and holds secure the tissue relative to the treatment device. Once the tissue is firmly secured to the suction head 60, the endoscope 12 is preferably withdrawn to a point where the scope tip is closer to the proximal end of the suction head 60. This facilitates observation of the cannula advancement step. The endoscope 12 may also be retracted just after the suction head tip 70 is placed near the ostium, but before the suction is applied to the tissue.

The cannulas 58 are now advanced into the tissue, seen in FIG. 21, below the surface as prescribed by the offset distance of the cannula tubes 52 to the face 62 of the suction head 60. The cannulas 58 of the electrode sets 54 may be activated by passage of electric current between them, which heats and ablates the tissue surrounding them and in between them, resulting in a heat affected zone 100. The heat-affected zone 100 is preferably concentrated at a depth in the tissue.

It is believed that afferent nerves emanating from the bladder trigone may be ablated to lessen the sensory signals driving overactive bladder.

In one preferred embodiment, the chosen depth of the heat-affected zone 100 is sufficient to protect the superficial layers of the bladder, such as the mucosa, from damage. In another preferred embodiment, the chosen depth is chosen to target superficial layers such as the suburothelium.

Preferably the electric current is in the radio-frequency range, and preferably it is delivered in a bi-polar fashion between the two electrodes. However, it is also contemplated that the two electrodes could form a mono-pole, and electric current could pass from them to a grounding pad, in a monopolar fashion. It is also contemplated, that a single electrode be utilized as a monopolar current source.

Multipolar configurations are also contemplated, either as single cannulas that are multipolar along their lengths or as multiple cannulas (3 or more) that are multiplexed or powered such that they operate in bi-polar modes, but possible in shifting patters. i.e., three cannulas that form 2 bipolar pairs (middle cannula is the common).

Once the treatment of the target location is performed, the suction may be released by venting the suction head 60 to atmosphere, the treatment device 20 may then be positioned in a different target location, and another ablation step may be performed, and repeated as many times as may be necessary to treat the bladder.

A number of different ablation patterns may be considered for treatment of the bladder. Such patterns are shown in FIGS. 22-31. Note that the patterns are shown relative to the surface, but are intended to be submucosal, as described above. The size of any one ablation zone may be affected by the device size, and the cannula diameter and exposed length, the spacing between the cannulas, the depth of the cannulas from the suction head face, and electrical parameters such as current, frequency, "on time", and other variables.

Figure 22:
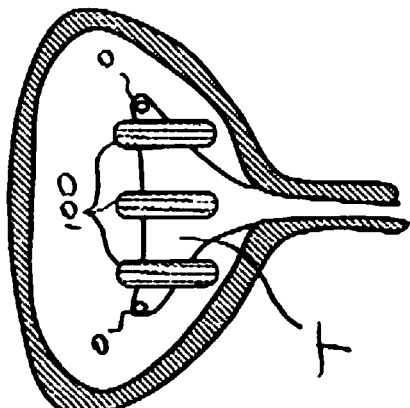

One aspect of the desired pattern may be simply the size of each ablation zone. A single ablation zone may be adequate if the size is large enough. However, a device that can yield a large ablation size may be too large for simple passage through the urethra. A device small enough to easily pass through the urethra may gain from multiple ablation zones, such as shown in FIG. 22. Here, three relatively parallel and evenly spaced zones 100 are created with three placement steps. A first zone 100a may be near one of the ostia O, a second zone 100b may be near the other ostium O, and a third zone 100c may be near the middle of the trigone T.

Figure 23:
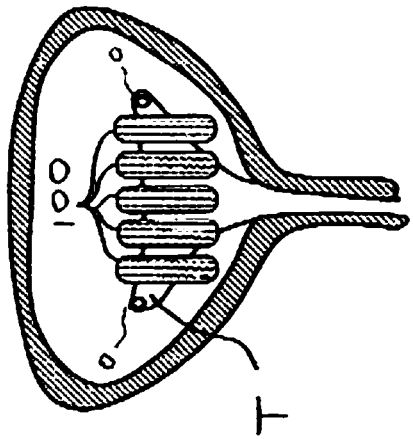
FIGS. 22-33 depict various ablation patterns made practicing an embodiment of a method of the invention.
Figure 24:
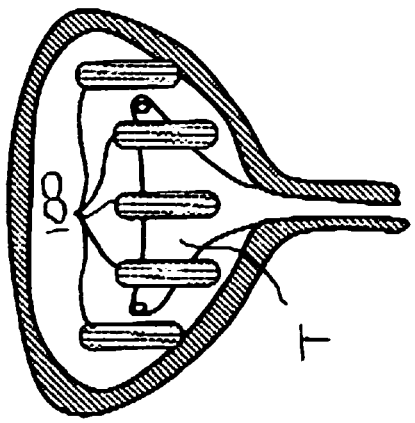

More or fewer ablation zones 100 are also contemplated, for example five, as shown in FIG. 23. While many of the nerves associated with OAB are believed to reside in the trigone, some may be lateral to the ureteral ostia, and as such ablating regions of the bladder lateral to or posterior to the ostia may be of further benefit, as illustrated in FIG. 24.

Figure 25:
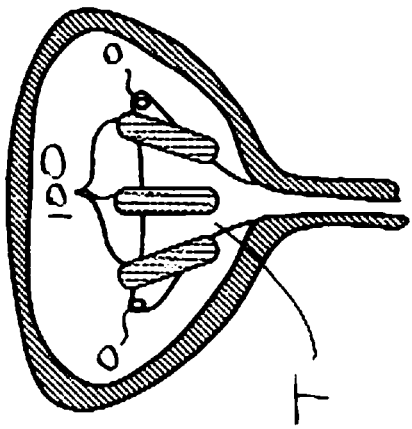

In addition to relatively parallel spacing of the ablation zones 100 (which may be performed by lateral manipulation of the treatment device, as the urethra and bladder are relatively soft pliable structures), it may be easier for the physician to pivot or pan the treatment device between ablation steps, resulting in a "fan shaped" pattern as shown in FIG. 25.

Figure 26:
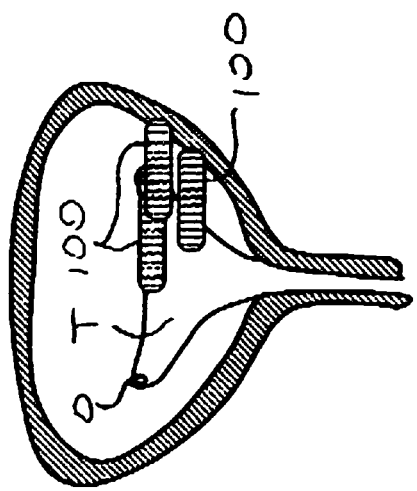

The nerves emanating from the trigone that are associated with OAB are further believed to coalesce near the ureteric ostia. FIG. 26 shows multiple concentrated ablation zones 100 near the ostium O.

Figure 27:
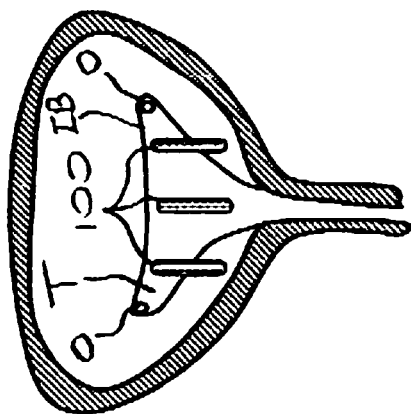

It is further contemplated that the distal portion of the treatment device, with the suction head and distal portions of the electrode tubes could be laterally articulable, and allow for more angled ablation zones 100, as illustrated in FIG. 27. Such an embodiment may be used with a flexible and articulable endoscope. Such angled or relatively horizontal ablation zones may be combined with more vertical ablation zones and/or fan shaped zones as described above.

Figure 28:
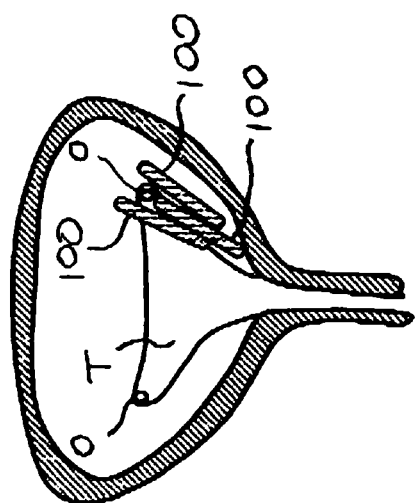

FIG. 28 shows a fan-shaped pattern of relatively narrow ablation zones 100. The fan-shape results from pivoting the device between ablations, as opposed to translating the device. A high number of zones 100 is created (FIG. 28 shows five but more are possible). The zones 100 preferably avoid going lateral of the ureteral ostia O.

Figure 29:
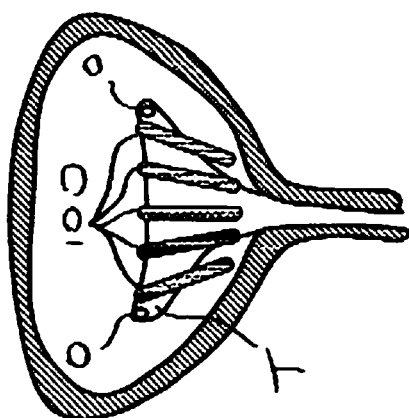

FIG. 29 shows a pattern of ablation zones 100 that avoids the inter-ureteric bar—the horizontal ridge between the ureteral ostia O. The zones 100 are shortened sufficiently to accomplish this goal.

Figure 30:
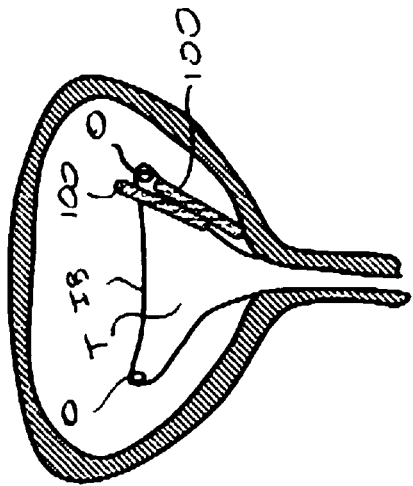

FIG. 30 shows a pattern of ablation zones 100 that encompasses both a fan-shape as well as avoiding the inter-ureteric bar. Again, the zones 100 are shortened sufficiently to avoid the inter-ureteric bar.

Figure 31:
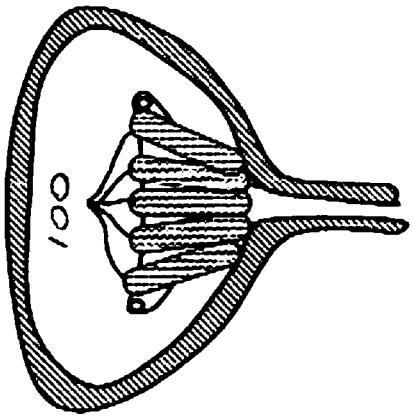

FIG. 31 shows a pattern of ablation zones 100 that is similar to the pattern shown in FIG. 26 but avoids the lateral burn to minimize the chance of causing trauma to the ureteral ostium O. This pattern may include other zones. The zones 100 shown in this Figure merely highlight those closest to the ostium O.

Figure 32:
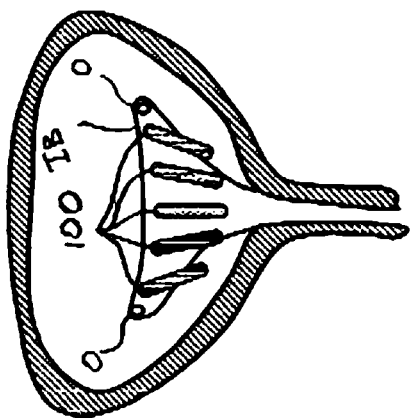
Figure 33:
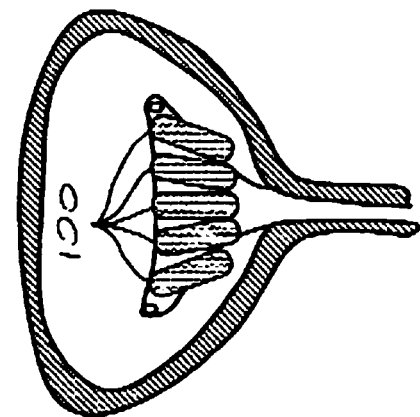

Making shorter ablation zones 100 may be accomplished using an electrode cannula having a shorter length of exposure L between the tip of the cannula 58 and the end of the insulation 59. FIGS. 32 and 33 show similar zone patterns except that the zones 100 in FIG. 32 are shorter than the zones 100 shown in FIG. 33. The zones 100 in FIG. 32 were made by a device shown in FIG. 34 having an exposure length L1 of approximately 10 mm. The zones 100 in FIG. 33 were made by a device shown in FIG. 35 having an exposure length L2 of approximately 15 mm.

As mentioned above, it may be desirable to create the ablation zone in the submucosal tissue, so as to spare the surface tissue and urothelium to minimize follow-up patient discomfort, risk of infection, and other benefits. In the treatment device embodiments described above, e.g. such as the embodiment shown in FIG. 10, the offset of the electrode tubes 52 from the face 62 of the suction head 60 influences the overall height/profile of the treatment device. Depending on the desired tissue depth for ablation, the height/profile of the treatment device could be larger than desired. An alternative embodiment that allows for relatively deep tissue depth, but minimizes impact on device profile is illustrated in FIGS. 36 and 37.

Figure 37:
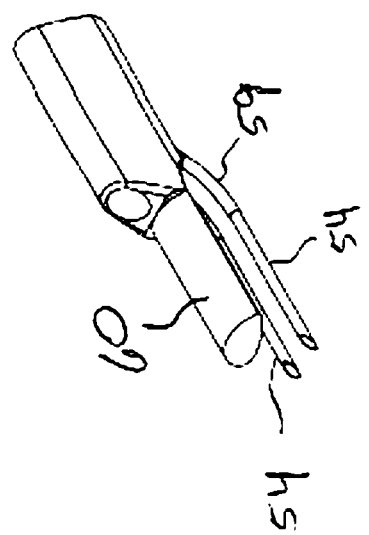
FIG. 37 is a perspective view of a distal end of an embodiment of the invention.
Figure 36:
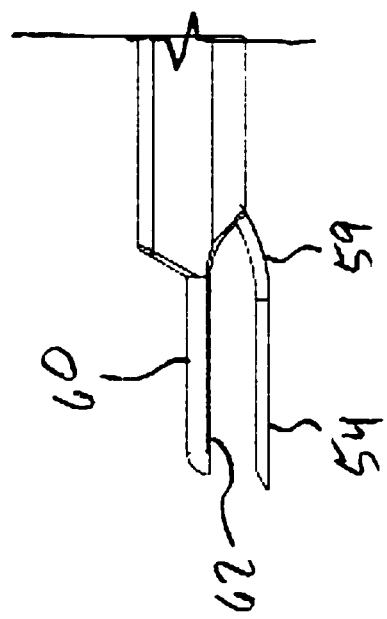
FIG. 36 is an elevation of a distal end of an embodiment of the invention.
Figure 38:
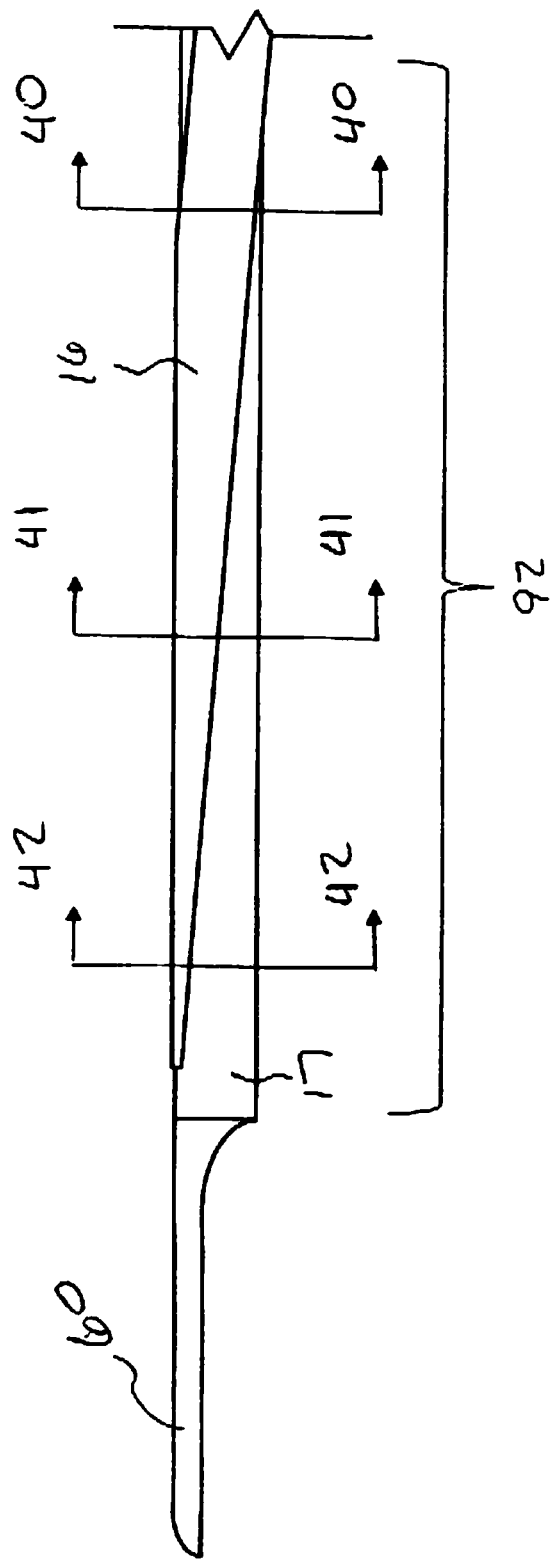
FIG. 38 is an elevation of an embodiment of the invention.

The embodiment shown in FIGS. 36 and 37 utilizes electrode sets/cannula 54 that may be pre-shaped to incorporate a curved design, for example, having an "S" shape near their distal ends or a general arcuate shape. When the electrodes 54 are advanced from the electrode tubes 52, they will angle down from the tube axis, thus embedding in tissue below the tube axis. This allows for the electrode tubes 52 to have a smaller offset distance from the face 62 of the suction head 60, which further allows for the treatment device 20 to have a smaller height/profile. Such cannula may be formed from an elastic material such as super elastic nickel titanium alloy, or other shapeable but elastic conductive materials.

Another embodiment that facilitates a lower profile/height device in the portion that passes through the urethra is illustrated in FIGS. 38-42. In contrast with the embodiment of FIGS. 7-9, where the endoscope channel or tube 16 extends alongside and parallel to the suction channel or tube 17, the alternative embodiment includes an endoscope tube 16 that resides at an angle α to the suction tube 17, and to the side of the suction tube. The endoscope tube may be cut along a plane near the top portion of the suction tube, so as to minimize the height of the treatment device. This is best illustrated in the section views 40 through 42.

Figure 39:
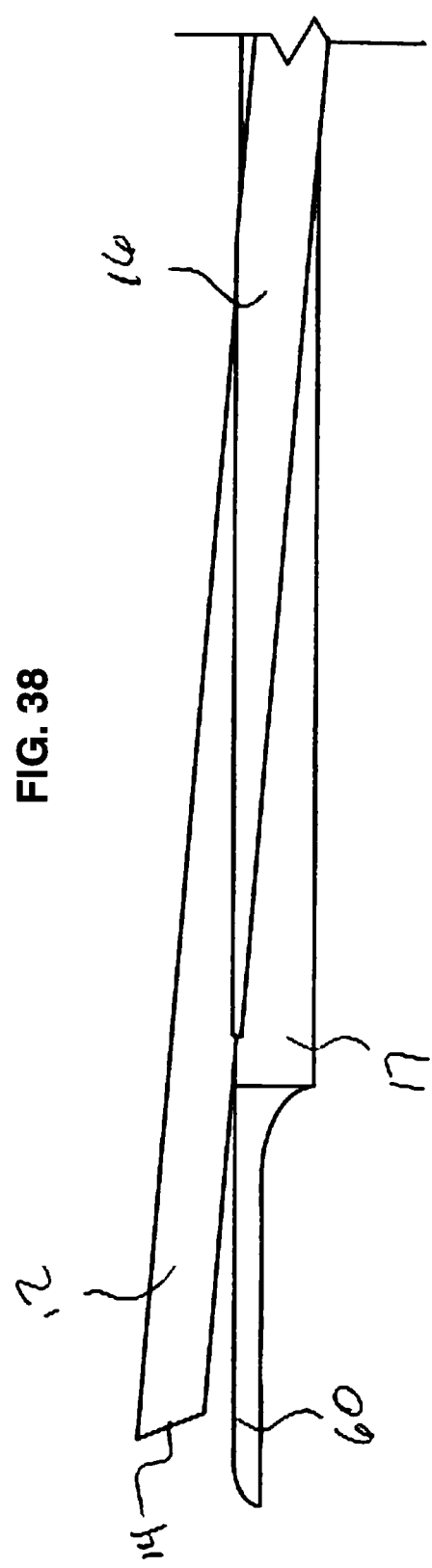
FIG. 39 is an elevation of an embodiment of the invention.
Figure 42:
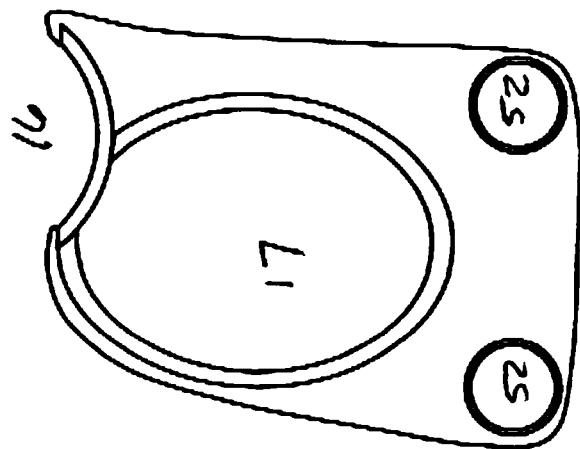
FIG. 42 is a sectional view of the embodiment of FIG. 38 taken along section lines 42-42.
Figure 41:
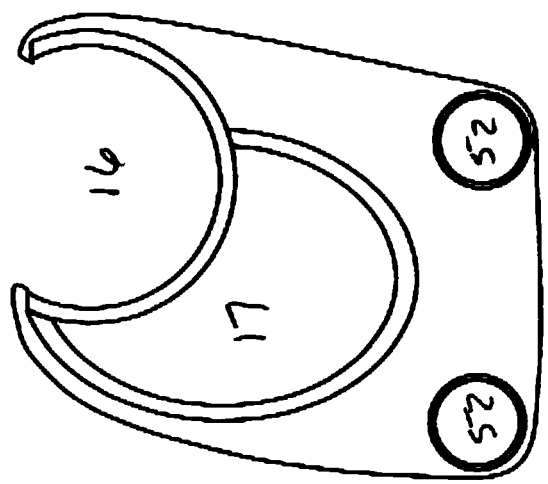
FIG. 41 is a sectional view of the embodiment of FIG. 38 taken along section lines 41-41.
Figure 40:
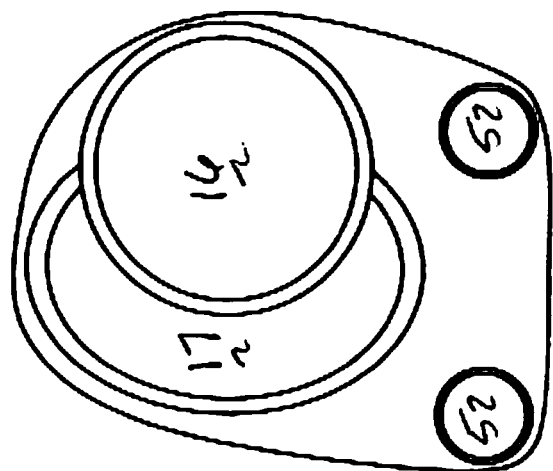
FIG. 40 is a sectional view of the embodiment of FIG. 38 taken along section lines 40-40.

At location 42, the suction tube 17 periphery is fully intact. To further minimize overall profile from side-to-side, the endoscope tube 16 may be "nested" into the suction tube 17 as shown, and the suction tube 17 may be ovalized to narrow the width. Proceeding distally on the treatment device, at section 43, the endoscope tube 16 resides higher within the suction tube 17, and the upper portion of the endoscope tube 16 is exposed, which maintains the vertical height of the treatment device in this area. Further distally, at section 44, the endoscope tube 16 rests even higher within the suction tube 17, and more of the endoscope tube 16 is exposed. Further distally there is not endoscope tube 16, as the endoscope 12 would project distally without any tubing surrounding it, as seen in FIG. 39, where the endoscope has been placed and extended above the distal aspect of suction head 60.

In use, this embodiment may be advanced "blindly" into the urethra until the suction head 60 is within the bladder, with the endoscope residing proximally, in the fully enclosed portion of the endoscope tube. This distal portion 92 of the device (FIGS. 40-42) is lower in profile than the comparable portion of the embodiment of FIGS. 7-9, as there is no endoscope tube nor endoscope in this portion during this delivery step.

At this point, the endoscope 12 can be advanced into the bladder and above the distal aspect of the suction head 60. Note also that the endoscope tip may be substantially spaced above the suction head 60, improving visualization, which may benefit the accurate placement of the suction head tip 70 relative to the ureteric ostia O.

Figure 43:
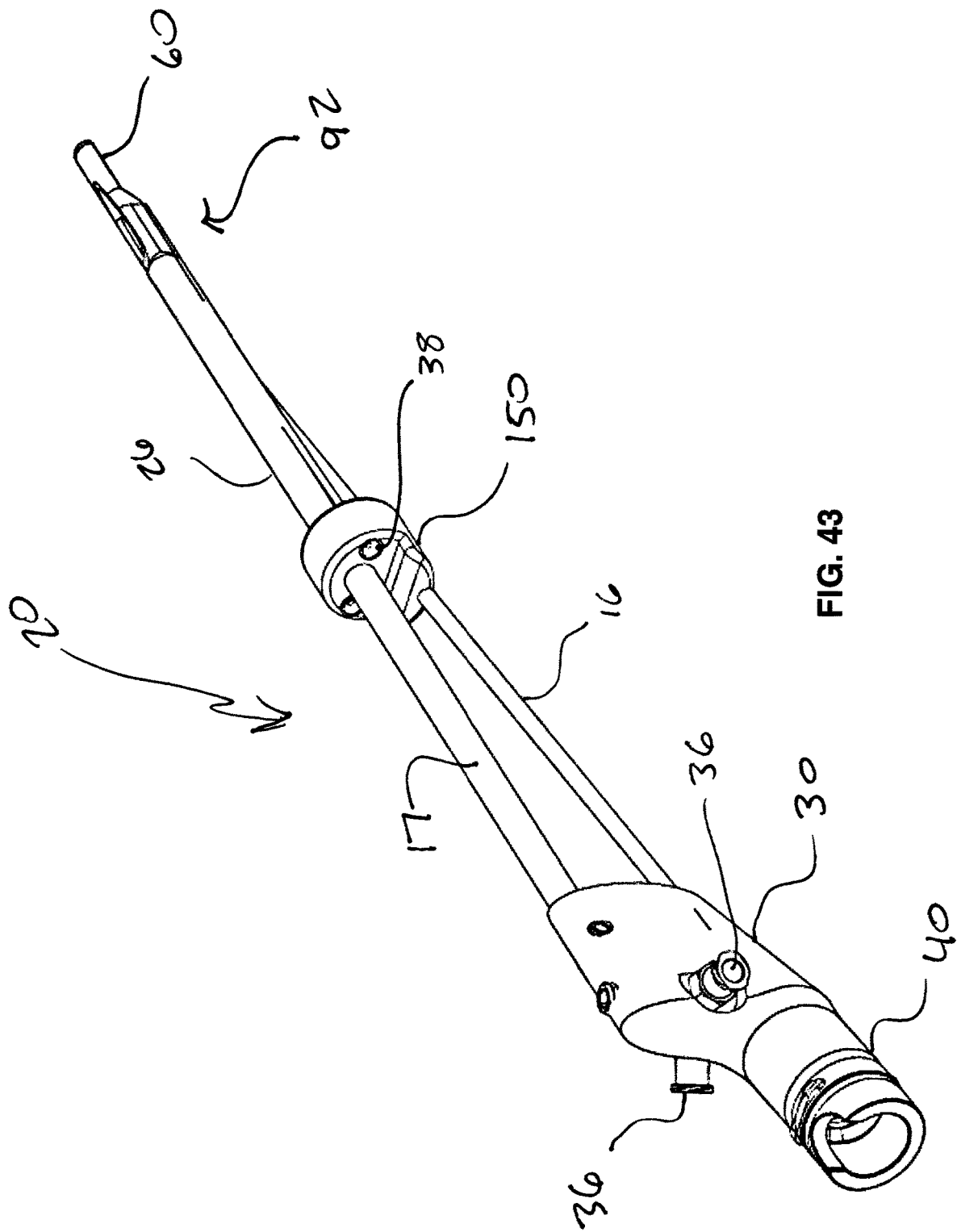
FIG. 43 is a perspective view of an embodiment of a device of the invention.

FIG. 43 illustrates a further embodiment of a treatment device 20 having a lower profile/height in the portion that extends into the urethra. Similar to the embodiment of FIGS. 38-42, this embodiment positions the endoscope 12 at an angle relative to the elongate shaft portion 26 of device 20.

Treatment device 20 includes an elongate suction tube 17 extending to the distal portion 92 and suction head 60. In this embodiment, the endoscope tube 16, is at an angle α (FIG. 46) to the suction tube 17. A handle assembly 30 may be connected to the proximal ends of these tubes to hold them relative to each other. An optional sliding tube 40 may be incorporated into the handle assembly 30 for connection of the endoscope 12 to the treatment device 20, similar to the sliding tube 40 described in previous embodiments. A sliding mechanism, which may be similar to the sliding mechanism 34 shown in FIGS. 4a and 5a and described above, may further be included to facilitate controlled advancement of the endoscope 12 relative to the treatment device 20. A connection hub 150 secured to the treatment device 20 proximal of the distal portion 92 preferably contains one or more receivers 38 to receive one or more electrode sets 54 (see, for example, FIG. 4a). One or more suction ports 36 may also be connected to the handle assembly 30, and are in fluid communication with the interior of the suction tube 17, for either irrigation, suction, and/or venting of the interior of suction tube 17 and suction head 60.

Figure 44:
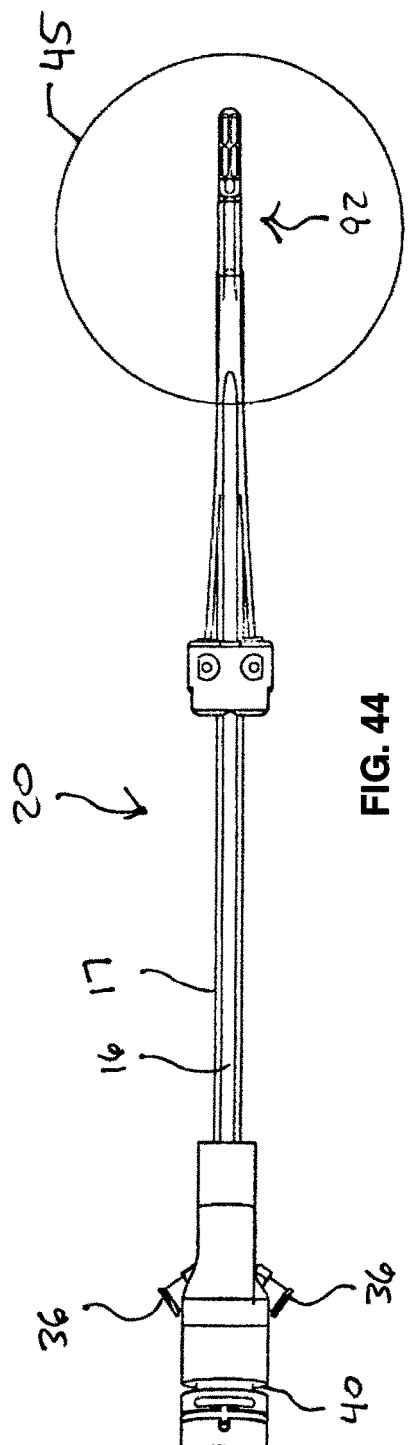
FIG. 44 is a bottom view of an embodiment of a device of the invention.
Figure 45:
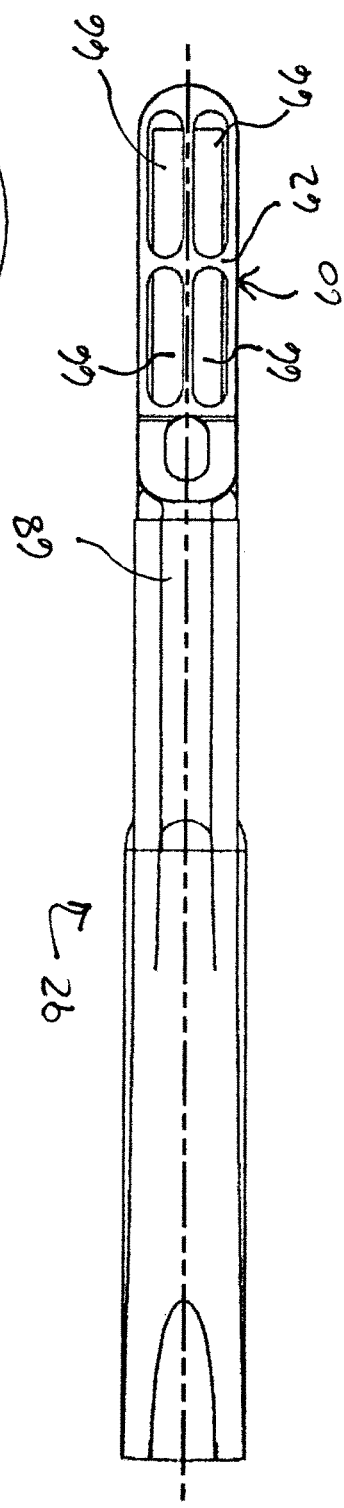
FIG. 45 is a detail view of cutout 45 of FIG. 44.

FIG. 44 is a bottom view of the treatment device 20, which shows the face 62 of the suction head 60. The suction head 60 is shown as including a plurality of apertures 66 leading to a suction chamber 68. These features are best seen in FIG. 45, which is a blow-up of area 45 showing the distal portion 92 of treatment device 20.

Figure 46A:
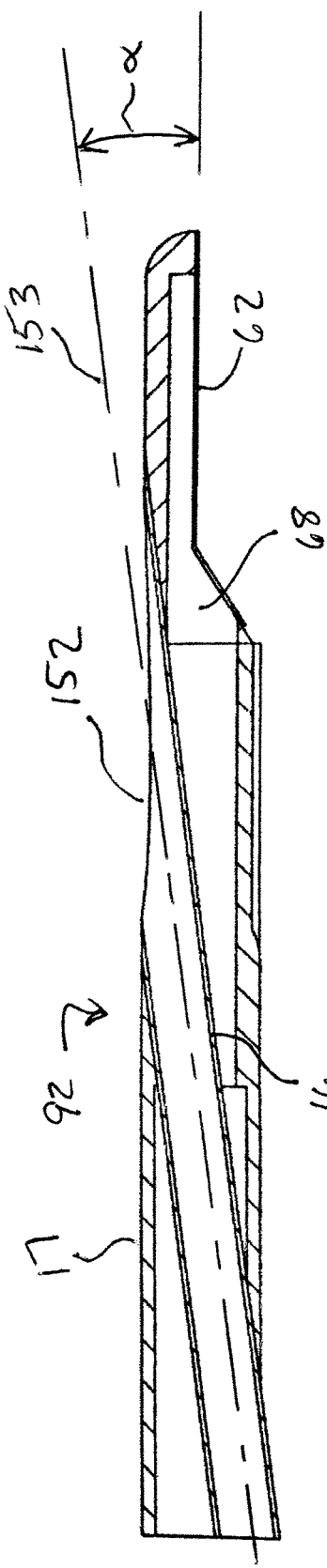
FIG. 46a is a cross-sectional view of a distal portion of an embodiment of the invention.

FIG. 46a is a longitudinal section view of the distal portion 92 of treatment device 20. Here it can be seen that the endoscope tube 16 has a longitudinal axis 153 that extends at an angle α to the face 62. It is to be understood that the endoscope tube 16 may be curved, in which case the angle α is measured to the longitudinal axis 153 at the opening 152. This may be described more accurately as measuring the angle between a tangent of a curved longitudinal axis at the opening 152 and the face 62.

The angle α is in the range of 1 to 20 degrees. The angle α may vary depending on the intended application. For example, when performing procedures via a relatively long urethra, a shallower angle α may be desired, for example in the range of 4 to 10 degrees. For female urethras of average length, good results have been achieved with an angle α of 6 to 8 degrees.

Figure 46B:
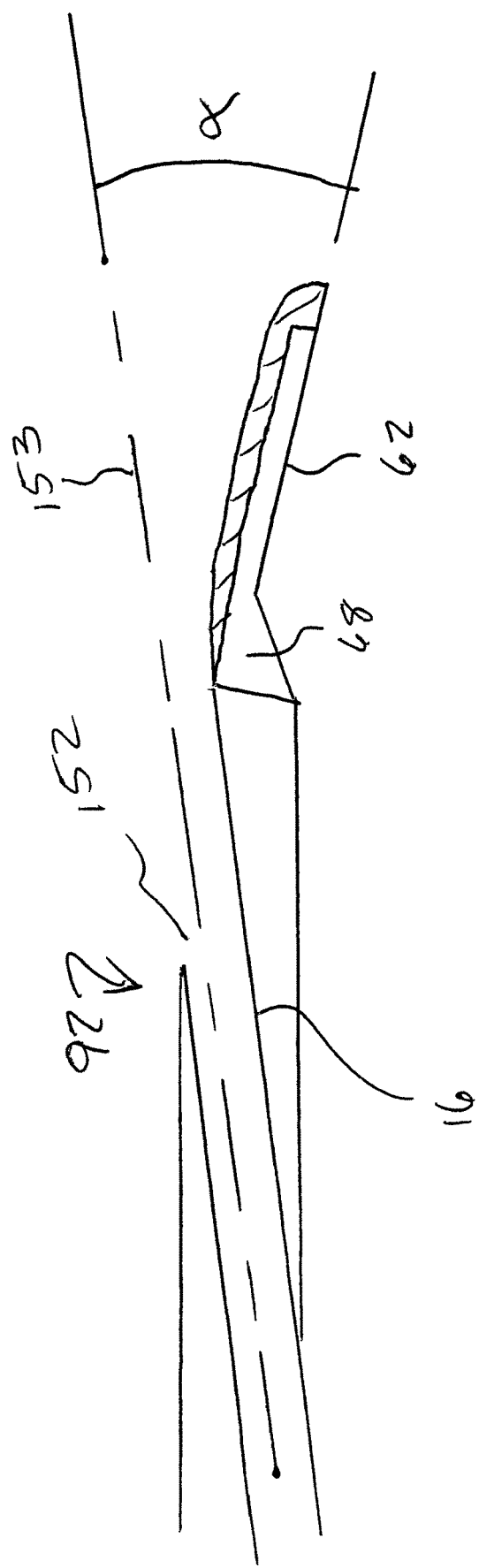
FIG. 46b is a cross-sectional view of a distal portion of an embodiment of the invention employing a tilted suction head.

FIG. 46b shows an embodiment where the suction face is tilted forward. It is envisioned that such an embodiment may include a suction face 62 that is tilted forward 5 to 10 degrees or more. If a tilted suction face 62 is employed, angle α may increase, or an endoscope tube 16 may be used that is parallel with the suction tube 17.

The distal opening 152 of the endoscope tube is preferably flush with the exterior surface of the suction tube 17 and tube holder 94, if present, so as to maintain a relatively low profile and smooth exterior surface to ease passage of the treatment device 20 into the urethra and into the bladder, when the endoscope 12 is in a retracted position.

FIG. 47 is a side view of the treatment device 20, with identifying locations of axial cross sectional views, 48-50.

FIG. 48 is a section view taken along section lines 48-48 of FIG. 47 and is just proximal of where the endoscope tube 16 intersects with the suction tube 17, at 170. Also visible here are the cross-sectional faces of the electrode tubes 52, which extend distally towards the tip. The endoscope tube 16 can be seen crossing the inside of the suction tube 17 further distally.

FIG. 49 is a section view taken along section lines 49-49 of FIG. 47 and is just proximal of where the endoscope tube 16 emerges from the upper surface of the suction tube 17. Further distally in this view, an aperture 66 is visible in the heel portion 63.

FIG. 50 is a section view taken along section lines 50-50 of FIG. 47 and is in the region of the device 20 where the endoscope tube 16 emerges to the outside. Portions of the wall of the endoscope tube 16 are removed, so as to provide a smooth and low profile surface to the distal portion 92. Also seen in this figure is an aperture 66, as well as the baffle 72 if present. Note that in this embodiment, there may not be a separate tube holder 94 as in some of the above described embodiments, but the suction tube 17 may be reshaped or have additional segments of differing shapes secured to it in the distal region. For example the shape may be more "squared off", as is shown, to facilitate incorporation and alignment of the electrode tubes 52, and to provide shape transition to the suction head 60.

The portions of intersection 170 between the endoscope tube 16 and suction tube 17 may be welded or similarly connected to secure the tubes together and provide a hermetic seal therebetween.

Figure 51:
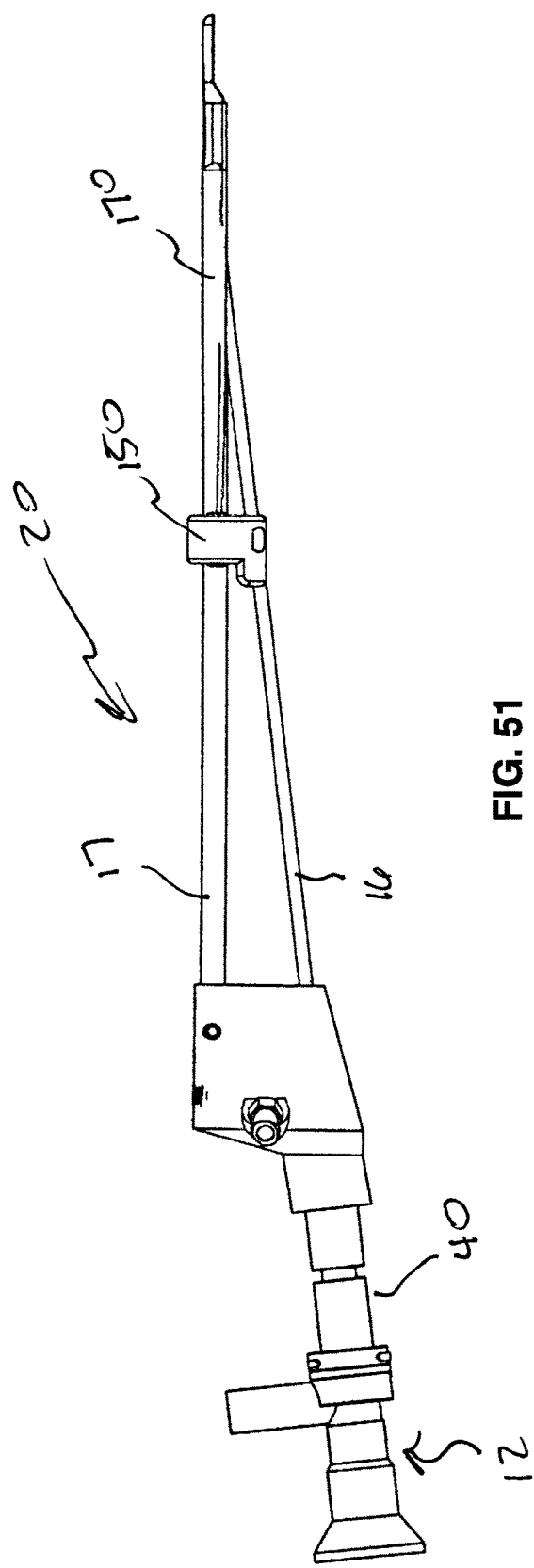
FIG. 51 is a side elevation of an embodiment of a device of the invention.
Figure 52:
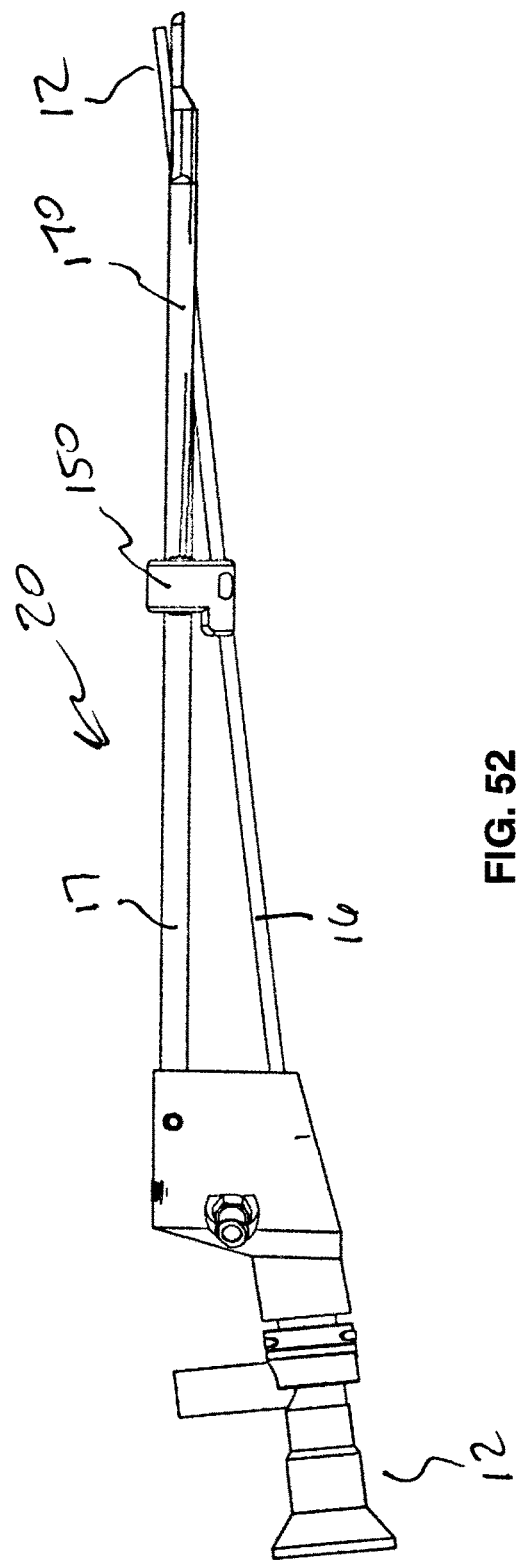
FIG. 52 is a side elevation of an embodiment of a device of the invention.

FIG. 51 shows a system 10 with a treatment device 20 as described in connection with the embodiments shown in FIGS. 43 through 47 above, together with an endoscope 12. In this figure, the endoscope is secured to the device 20, and in a retracted position. Note that the profile of the distal portion 92 of device 20 is low profile, suitable for advancement through the urethra and into the bladder space. Once the device 20 is in the bladder, the endoscope 12 may be advanced (FIG. 52), in order to view the placement of the suction head 60 in one or more desired locations, as described above in connection with the various embodiments described previously.

Figure 55:
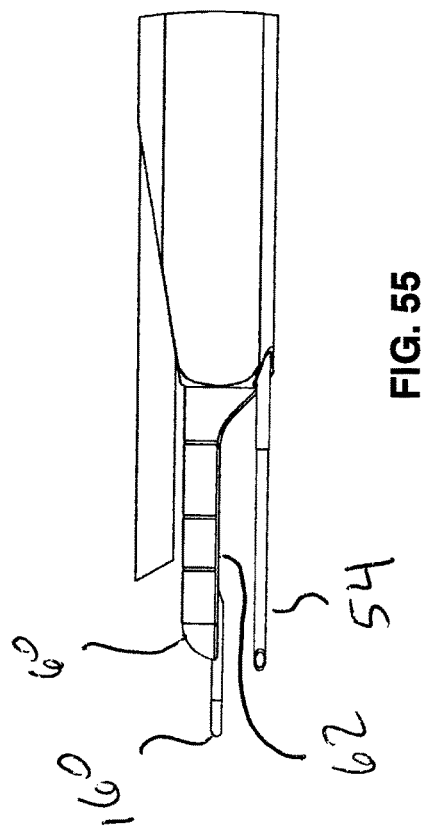
FIG. 55 is a perspective view of an embodiment of a distal end of a device of the invention.
Figure 53:
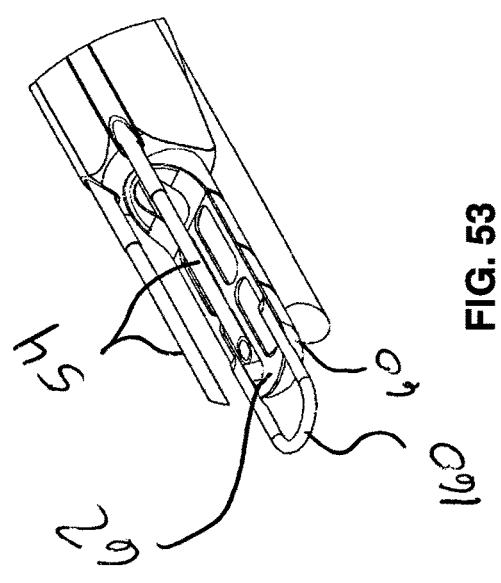
FIG. 53 is a perspective view of an embodiment of a distal end of a device of the invention.
Figure 54:
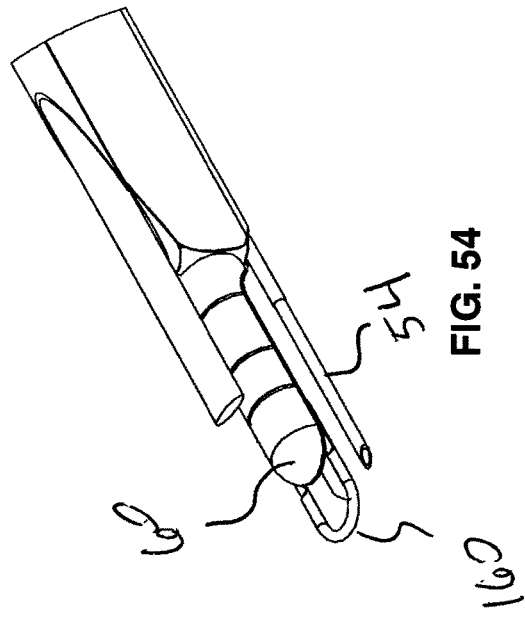
FIG. 54 is a side elevation of an embodiment of a distal end of a device of the invention.

FIGS. 53 through 55 show an embodiment similar to embodiments described above, such as, for example, the embodiment described in connection with FIG. 14. A positioning feature 160, shown in this embodiment as a hoop, is attached near the distal end of the suction head 60. Positioning feature 160 may be attached to the face 62, and may be fabricated of any suitable material that can be secured to the face 62. For example, the hoop 160 may be a metallic, such as stainless steel, and may be welded, brazed, soldered, or bonded to the face 62 with adhesive. Other materials are contemplated, including polymeric and elastomeric materials. For example, the hoop may be made of a flexible material to ensure that it is atraumatic. Though a hoop is shown, the positioning feature 160 may take the form of one or more pointers, cross hairs, a circle, a wedge, or any other shape useful in providing a visual guide.

The positioning feature 160 may be used to aid in the placement of the device 20 relative to the desired anatomy to be treated. For example, to position the suction head 60 in a desired position relative to a uretic ostium in the bladder, the positioning feature 160 may be visualized with an endoscope 12 and visually lined up with the ostium. This can help assure that when the electrodes 54 are extended into the tissue, they will end up a desired distance from the ostium, such that when they are activated, they don't adversely affect the tissue of the ureter or its ostium.

In one embodiment, when the ostium is viewed with the endoscope, and the ostium is centered within the positioning feature 160, the hoop is sized such that the extended electrodes 54 are close but not at the ostial tissue.

The positioning hoop 160 may optionally be added to any of the above described embodiments of the treatment device 20.

As mentioned above, in connection with the embodiments of FIG. 10, a 30 degree downward looking angled endoscope may be preferable, as is an offset spacing of the endoscope above the suction head, to aid in accurate and relatively unobstructed positioning of the suction head. This is the case with a conventional Hopkins rod type of endoscope.

Figure 56:
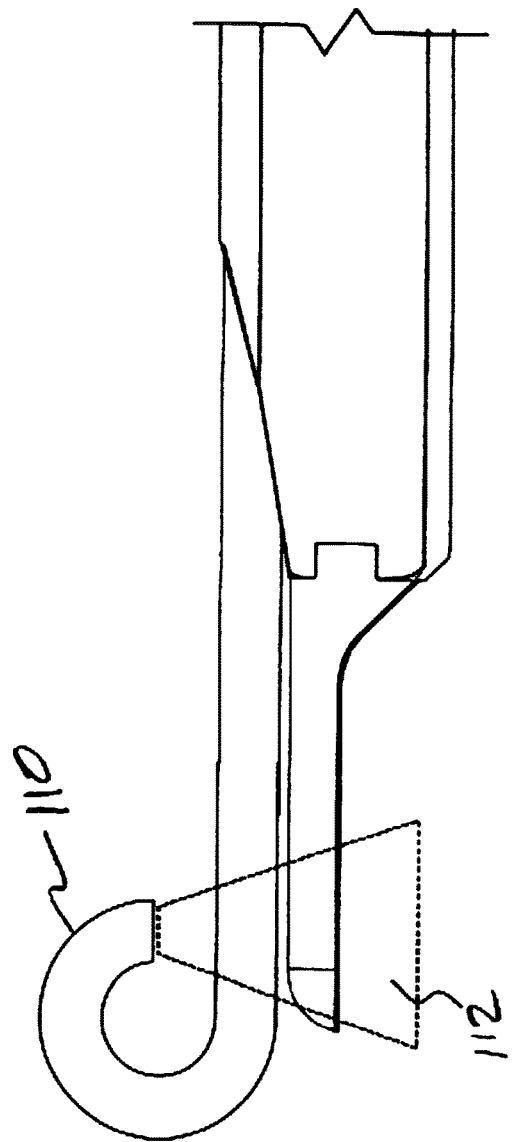
FIG. 56 is an elevation view of a distal end of an embodiment of the invention being used with a flexible embodiment of an endoscope; and, FIG. 57 is an elevation view of a distal end of an embodiment of the invention being used with an articulated embodiment of an endoscope.

Alternatively, a flexible deflectable endoscope may be utilized, as shown in FIG. 56. The treatment device 20 may be any of the above described embodiments, such as that described in connection with FIG. 10, but utilizing a flexible deflectable endoscope 110 as shown. Once entry into the bladder has been made, the endoscope 110 is deflected to view in a downward direction, preferably a significant distance above the suction head, as shown. The viewing field 112 is indicated by the dashed line.

If a deflectable scope is used, the need for the offset of the endoscope tube as described in connection with FIG. 10 would not be as important, thus providing an opportunity to further lower the height of the treatment device.

Figure 57:
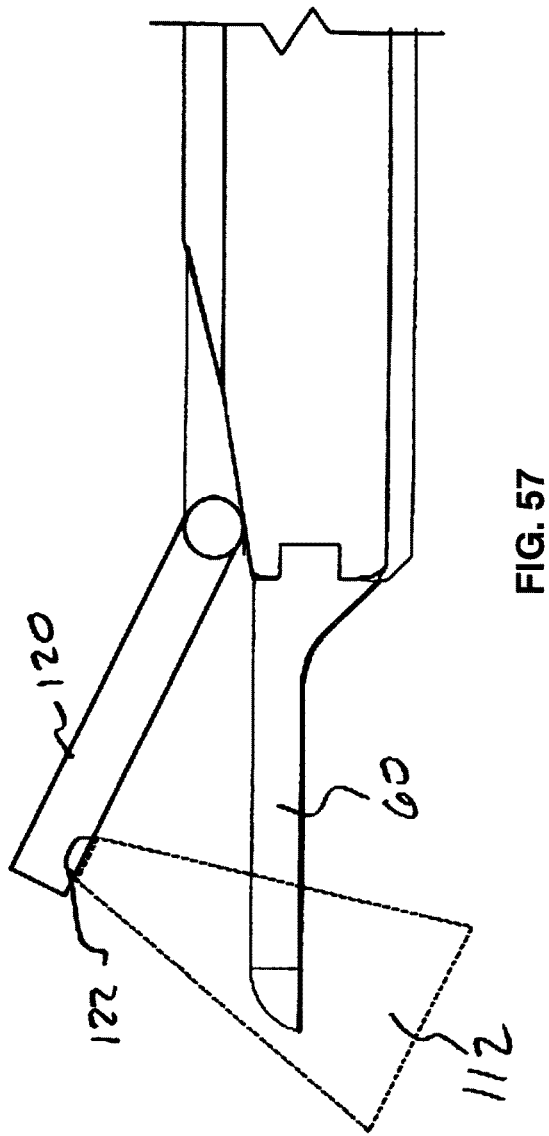

Alternatively, an articulating endoscope 120 such as indicted in FIG. 57 may be utilized to enhance the visualization of the treatment device. One such articulating endoscope may have a side-facing camera 122 built into the deflecting tip portion. The height and angle of the image relative to the suction head may be altered by articulating the distal tip portion.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An energy delivery apparatus configured to modulate bladder function, the apparatus comprising:
   an elongate shaft having a distal portion sized to be inserted through a human urethra and into a bladder, the shaft comprising first and second electrode lumens extending along a longitudinal axis of the shaft;
   a suction head coupled to a distal end of the shaft and comprising a first surface defining a first plane and one or more suction apertures;
   a first electrode positioned in the first electrode lumen, the first electrode comprising an intermediate portion and a distal portion extending distally from the intermediate portion; and
   a second electrode positioned in the second electrode lumen, the second electrode comprising an intermediate portion and a distal portion extending distally from the intermediate portion,
   wherein the first and second electrodes are longitudinally movable relative to the respective first and second electrode lumens between:
   (i) a retracted configuration, in which the intermediate and distal portions of the first and second electrodes are fully contained within the respective first and second electrode lumens, and
   (ii) a deployed configuration, in which the intermediate and distal portions of the first and second electrodes are fully extended out respective distal end openings of the first and second electrode lumens, and
   wherein, when the first and second electrodes are in the deployed configuration, the intermediate portion of each of the first and second electrodes has a curved configuration, and the distal portion of each of the first and second electrodes has a straight configuration and extends within a second plane that is parallel with the first plane.

2. The apparatus of claim 1, wherein, when the first and second electrodes are in the retracted configuration, the intermediate portion of each of the first and second electrodes is constrained in a linear configuration within the respective first and second electrode lumens.

3. The apparatus of claim 1, wherein the first and second electrodes each comprises an elastic shape-memory material that facilitates the intermediate portions to elastically reconfigure from linear to curved when the first and second energy delivery electrodes reconfigure from the retracted configuration to the deployed configuration.

4. The apparatus of claim 1, further comprising an electrically insulative material covering on the respective intermediate portions of the first and second electrodes.

5. The apparatus of claim 1, wherein the suction head further comprises an angled face adjacent to and proximal of the first surface, the angled face defining at least one suction aperture, and wherein an obtuse angle is defined between the angled face and the first surface.

6. The apparatus of claim 5, wherein the angled face is disposed between the first surface and the distal end openings of the first and second electrode lumens.

7. The apparatus of claim 1, wherein, when the distal portion of the shaft is positioned in a bladder such that the first surface of the suction head is in contact with a mucosal tissue surface of a trigone region of the bladder wall, and the first and second electrodes are moved from the retracted configuration to the deployed configuration, the first and second electrodes are configured to deliver energy along the second plane to non-superficial target tissue within the trigone region of the bladder wall to thereby modulate bladder function while retaining the mucosal surface of the bladder wall superficial to the non-superficial target tissue substantially intact.

8. The apparatus of claim 1, wherein the shaft comprises a scope channel configured to receive a visualization device for providing visual confirmation of placement of the suction head at a targeted tissue surface.

9. The apparatus of claim 8, wherein the shaft comprises one or more sealed suction channels in fluid communication with the one or more suction apertures in the first surface of the suction head.

10. The apparatus of claim 1, further comprising a handle assembly attached to a proximal end portion of the shaft, the handle assembly comprising a first actuator operatively coupled to the first and second electrodes and configured to move the first and second electrodes between the retracted configuration and the deployed configuration.

11. The apparatus of claim 10, the handle assembly further comprising a second actuator configured to selectively electrically couple the first and second electrodes with an electrical energy source.

12. The apparatus of claim 11, further comprising
a first interlock that prevents the first and second electrodes from being moved from the retracted configuration to the deployed configuration unless a pressure indicates that a mucosal tissue surface is being retained by the one or more suction apertures of the first surface, and
a second interlock that prevents the first and second electrodes from being coupled to the electrical energy source unless the first and second electrodes are in the deployed configuration.

13. An energy delivery apparatus configured to modulate bladder function, the apparatus comprising:
an elongate shaft having a distal portion sized to be inserted through a human urethra and into a bladder, the shaft comprising first and second electrode lumens extending along a longitudinal axis of the shaft;
a suction head coupled to a distal end of the shaft and comprising a first surface having one or more suction apertures;
a first electrode positioned in the first electrode lumen, the first electrode comprising an intermediate portion and a distal portion extending distally from the intermediate portion; and
a second electrode positioned in the second electrode lumen, the second electrode comprising an intermediate portion and a distal portion extending distally from the intermediate portion,
wherein the first and second electrodes are longitudinally movable relative to the respective first and second electrode lumens between:
(i) a retracted configuration, in which the intermediate and distal portions of the first and second electrodes are fully contained within the respective first and second electrode lumens, and
(ii) a deployed configuration, in which the intermediate and distal portions of the first and second electrodes are fully extended out respective distal end openings of the first and second electrode lumens,
wherein, when the first and second electrodes are in the deployed configuration, the intermediate portion of each of the first and second electrodes has a curved configuration, and the distal portion of each of the first and second electrodes has a straight configuration, and
wherein a cross-sectional profile of a distal end portion of the device expands when the first and second electrodes transition from the retracted configuration to the deployed configuration.

14. The apparatus of claim 13, wherein the first and second electrodes each comprises an elastic shape-memory material that facilitates the intermediate portions to elastically reconfigure from linear to curved when the first and second energy delivery electrodes reconfigure from the retracted configuration to the deployed configuration.

15. The apparatus of claim 13, further comprising an electrically insulative material covering on the respective intermediate portions of the first and second electrodes.

16. The apparatus of claim 13, wherein the suction head further comprises an angled face adjacent to and proximal of the first surface, the angled face defining at least one suction aperture, and wherein an obtuse angle is defined between the angled face and the first surface.

17. The apparatus of claim 13, wherein, when the distal portion of the shaft is positioned in a bladder such that the first surface of the suction head is in contact with a mucosal tissue surface of a trigone region of the bladder wall, and the first and second electrodes are moved from the retracted configuration to the deployed configuration, the first and second electrodes are configured to deliver energy along the second plane to non-superficial target tissue within the trigone region of the bladder wall to thereby modulate bladder function while retaining the mucosal surface of the bladder wall superficial to the non-superficial target tissue substantially intact.

18. The apparatus of claim 13, wherein the shaft comprises
a scope channel configured to receive a visualization device for providing visual confirmation of placement of the suction head at a targeted tissue surface, and
one or more sealed suction channels in fluid communication with the one or more suction apertures in the first surface of the suction head.

19. The apparatus of claim 13, further comprising a handle assembly attached to a proximal end portion of the shaft, the handle assembly comprising
a first actuator operatively coupled to the first and second electrodes and configured to move the first and second electrodes between the retracted configuration and the deployed configuration, and
a second actuator configured to selectively electrically couple the first and second electrodes with an electrical energy source.

20. The apparatus of claim 19, further comprising
a first interlock that prevents the first and second electrodes from being moved from the retracted configuration to the deployed configuration unless a pressure indicates that a mucosal tissue surface is being retained by the one or more suction apertures of the first surface, and a second interlock that prevents the first and second electrodes from being coupled to the electrical energy source unless the first and second electrodes are in the deployed configuration.

\* \* \* \* \*